(12) United States Patent
Freitag et al.

(10) Patent No.: US 12,130,227 B2
(45) Date of Patent: Oct. 29, 2024

(54) SYSTEMS AND METHODS FOR BIO-INACTIVATION

(71) Applicant: Excelitas Technologies Corp., Waltham, MA (US)

(72) Inventors: John Christopher Freitag, Lake Oswego, OR (US); Theresa Thompson, West Linn, OR (US); Garth Eliason, Hood River, OR (US); Jay Pasquantonio, Damascus, OR (US)

(73) Assignee: Excelitas Technologies Corp., Waltham, MA (US)

( * ) Notice: Subject to any disclaimer, the term of this patent is extended or adjusted under 35 U.S.C. 154(b) by 1058 days.

(21) Appl. No.: 17/064,775

(22) Filed: Oct. 7, 2020

(65) Prior Publication Data

US 2021/0018429 A1 Jan. 21, 2021

Related U.S. Application Data

(62) Division of application No. 15/783,428, filed on Oct. 13, 2017, now Pat. No. 11,747,266.

(Continued)

(51) Int. Cl.
*G01N 21/01* (2006.01)
*A61L 2/10* (2006.01)
(Continued)

(52) U.S. Cl.
CPC .............. *G01N 21/01* (2013.01); *A61L 2/10* (2013.01); *B01L 13/02* (2019.08); *C12M 23/48* (2013.01);

(Continued)

(58) Field of Classification Search
None
See application file for complete search history.

(56) References Cited

U.S. PATENT DOCUMENTS

| 7,687,785 | B2 | 3/2010 | Chen |
| 8,277,734 | B2 | 10/2012 | Koudymov et al. |

(Continued)

FOREIGN PATENT DOCUMENTS

| CN | 101215017 A | 7/2008 |
| CN | 101238073 A | 8/2008 |

(Continued)

OTHER PUBLICATIONS

ISA Korean Intellectual Property Office, International Search Report and Written Opinion Issued in Application No. PCT/US2017/056566, Jan. 30, 2018, WIPO, 12 pages.

(Continued)

*Primary Examiner* — Matthew D Krcha
*Assistant Examiner* — Brittany I Fisher
(74) *Attorney, Agent, or Firm* — Wolf, Greenfield & Sacks, P.C.

(57) ABSTRACT

A system for irradiating a microplate may include a modular light engine with one or more light emitting devices. The light emitting devices are configured to emit germicidal radiation to irradiate the microplate, which is configured to be positioned below the modular light engine inside a chamber of the microplate irradiation system. In this way, a uniform intensity of germicidal radiation may be output by light emitting devices, resulting in disruption of contaminating nucleic acids present in the microplate.

13 Claims, 15 Drawing Sheets

Related U.S. Application Data

(60) Provisional application No. 62/412,030, filed on Oct. 24, 2016.

(51) Int. Cl.
  *C12M 3/00* (2006.01)
  *G01N 21/64* (2006.01)
  *B01L 3/00* (2006.01)
  *B01L 9/00* (2006.01)
  *C12M 1/12* (2006.01)
  *G06V 20/69* (2022.01)

(52) U.S. Cl.
  CPC .............. *B01L 3/5085* (2013.01); *B01L 9/523* (2013.01); *B01L 2300/0829* (2013.01); *C12M 37/00* (2013.01); *G01N 2021/646* (2013.01); *G06V 20/69* (2022.01)

(56) References Cited

U.S. PATENT DOCUMENTS

| | | |
|---|---|---|
| 9,061,082 B2 | 6/2015 | Gaska et al. |
| 2006/0188389 A1 | 8/2006 | Levy |
| 2006/0261291 A1 | 11/2006 | Gardner, III |
| 2009/0314308 A1 | 12/2009 | Kim et al. |
| 2013/0214174 A1 | 8/2013 | Domenig et al. |
| 2013/0270445 A1 | 10/2013 | Gaska et al. |
| 2015/0221844 A1* | 8/2015 | Tahara ................. H01L 27/153 250/492.1 |
| 2016/0093412 A1 | 3/2016 | Liao et al. |
| 2016/0106873 A1* | 4/2016 | Dobrinsky ......... G01N 21/6456 250/393 |
| 2016/0184467 A1 | 6/2016 | Cheng et al. |
| 2016/0249436 A1 | 8/2016 | Inskeep |
| 2016/0271281 A1 | 9/2016 | Clynne et al. |
| 2016/0324996 A1 | 11/2016 | Bilenko et al. |
| 2017/0100494 A1 | 4/2017 | Dobrinsky et al. |
| 2018/0055959 A1 | 3/2018 | Lin et al. |
| 2018/0113066 A1 | 4/2018 | Freitag et al. |
| 2018/0280723 A1 | 10/2018 | Enwemeka et al. |
| 2018/0339073 A1 | 11/2018 | Clynne et al. |

FOREIGN PATENT DOCUMENTS

| | | |
|---|---|---|
| CN | 102210882 A | 10/2011 |
| CN | 102861348 A | 1/2013 |
| CN | 103392006 A | 11/2013 |
| CN | 104707158 A | 6/2015 |
| CN | 204613083 U | 9/2015 |
| CN | 104971789 A | 10/2015 |
| CN | 105709258 A | 6/2016 |
| CN | 107921158 A | 4/2018 |
| WO | 9743915 A1 | 11/1997 |
| WO | 2004031706 A1 | 4/2004 |
| WO | 2014036080 A1 | 3/2014 |

OTHER PUBLICATIONS

State Intellectual Property Office of the People's Republic of China, Office Action and Search Report Issued in Application No. 201780065411.0, Aug. 4, 2020, 25 pages. (Submitted with Partial Translation).

Mori et al., Development of a new water sterilization device with a 365 nm UV-LED. Medical & biological engineering & computing. Dec. 2007;45:1237-41.

* cited by examiner

SYSTEMS AND METHODS FOR BIO-INACTIVATION

CROSS REFERENCE TO RELATED APPLICATIONS

The present application is a divisional of U.S. Non-Provisional Patent application Ser. No. 15/783,428, entitled "SYSTEMS AND METHODS FOR BIO-INACTIVATION", and filed on Oct. 13, 2017. U.S. Non-Provisional patent application Ser. No. 15/783,428 claims priority to U.S. Provisional Application No. 62/412,030 entitled "MICROPLATE IRRADIATION SYSTEM", and filed on Oct. 24, 2016. The entire contents of which are hereby incorporated by reference for all purposes.

BACKGROUND/SUMMARY

Clinical and laboratory settings require sterilization of equipment to eradicate microorganisms, protein, and/or nucleic acid contaminants. Methods for inactivation of biological microorganisms and contaminants currently in use are either chemical-based or illumination-based. While many microorganisms and contaminants are easily removed or inactivated using standard chemical disinfection methods (e.g., bleach, alcohol); some microorganisms are resistant to standard sterilization techniques. Additionally, some enzymes found in living cells and biological fluids may act as molecular contaminants (e.g., ribonuclease enzymes or RNase A), and may be highly resistant to denaturation. Furthermore, chemical-based disinfection methods may not be suitable for use with certain surfaces/materials and may not affect irreversible inactivation.

The inventors herein recognize the forgoing issues and propose methods to partially address them. In an example approach, a microplate irradiation system includes a bio-inactivation device comprising a modular light engine with one or more light emitting devices, where each light emitting device may include an array of light emitting diodes configured to emit germicidal radiation. In one embodiment, the germicidal radiation may be directed towards a microplate inserted directly below the modular light engine inside a chamber of the bio-inactivation device. The microplate may contain a liquid reagent mixture and when positioned below the modular light engine, may receive a uniform intensity of germicidal radiation (e.g., ultraviolet light) from the array of light emitting diodes, resulting in disruption of contaminants present in the reagent mix.

In this way, reagents dispensed in a microplate may be sterilized by introducing the microplate in a bio-inactivation device, including a modular light emitting engine with a plurality of light emitting diodes emitting germicidal radiation. Emission from the a modular light engine is incident on the microplate at a (relatively) uniform spatial intensity, which disrupts the contaminating nucleic acids in the reagent mix, making the reagent suitable for subsequent nucleic acid sequencing and/or amplification protocols.

In another example, a bio-inactivation device comprising a modular light engine with one or more light emitting devices configured to emit germicidal radiation may be configured as a composite hand-held illumination unit for disinfection of surfaces (e.g., lab benches and hoods), glassware, etc., without the microplate attachment. Herein, the bio-inactivation device may be configured to emit germicidal radiation directed towards surfaces and materials to be treated (e.g., disinfected). The spatio-temporal emission pattern from the hand-held bio-inactivation unit may be regulated by a controller either manually (by user input) or automatically based on feedback from one or more sensors in the bio-inactivation unit. In one example, the unit may include a closed loop control system using a photodetector to measure reflectance from the surface before and after treatment. In another example, the closed loop control system comprising the photodetector may measure fluorescence of the surface before and after treatment. In the embodiments described above, an inactivation unit may be used to emit germicidal radiation of a single specific wavelength that effectively targets biological organisms and/or targets contaminating nucleic acids by disrupting their DNA structure. Alternatively, the device may output a combination of two or more wavelengths to enable permanent and complete inactivation by targeting different aspects of the organisms.

In this way, a compact bio-inactivation unit combined with a photodetector may be used as a point-of-use device to treat surfaces for disinfection. The device may initially measure the surface reflectance and/or irradiance prior to germicidal radiation, followed by exposure to germicidal radiation of one or multiple wavelengths and subsequent re-measurement of the surface reflectance and/or fluorescence to determine the level of inactivation efficacy. A more complete and efficient inactivation of biological contaminants may therefore be achieved using multiple wavelengths of light with concurrent real time feedback based on the change in surface reflectance and/or fluorescence properties.

The advantages and features of the present description are captured in the following detailed description; either singularly or in connection with the accompanying drawings.

It is to be understood that the summary above is provided to introduce a simplified selection of concepts that are described further in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
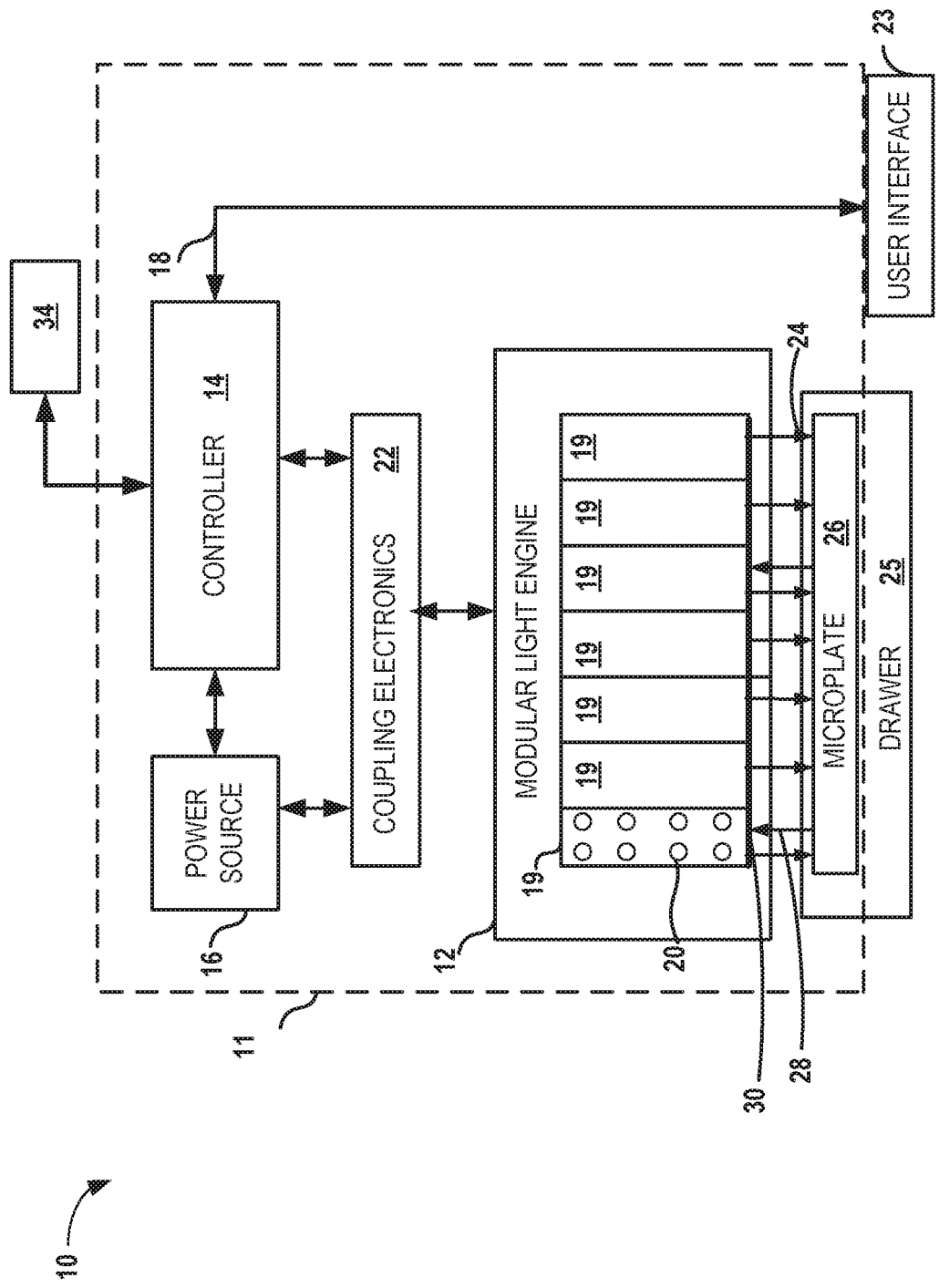
FIG. 1 illustrates a schematic of a first embodiment of a bio-inactivation unit in the form of a microplate irradiation system.

The present description relates to methods and systems for inactivation of biological organisms and other molecular contaminants, comprising a bio-inactivation device with a modular light emitting engine and optionally with a cavity/drawer configured to house a microplate, for sterilizing reagents and surfaces by radiation, such as UV-C radiation.

As described above, sterilization of clinical and/or laboratory settings may include chemical- or illumination-based techniques that can insufficiently target desired organisms or enzymes. These techniques may suffer from additional issues. For example, illumination-based methods of inactivation may employ conventional lamps (e.g., gas-discharge lamps or mercury arc), which may afford higher efficacy than chemical methods, but may be incapable of determining the efficacy of bio-inactivation. Additionally, lamp-based UV systems may be expensive and cumbersome, have short lifetimes, and include a warm-up period to attain stable output, making them impractical for daily use.

An example approach involves UV germicidal irradiation as an illumination-based disinfection method that uses short-wavelength UV (i.e. UVC) light to inactivate microorganisms. Ultraviolet (UV) radiation ranges from 100-400 nm with four distinct spectral regions including; vacuum UV (100-200 nm), UVC (200-280 nm), UVB (280-315 nm), and UVA (315-400 nm). A mechanism of UVC inactivation of biological microorganisms is cellular damage caused by disruption (distortion) of their nucleic acid structure when UVC is absorbed. The UVC spectrum, especially in the range of 250-270 nm with 265 nm being the peak germicidal wavelength, is commonly known as germicidal UV as it is strongly absorbed by the nucleic acids of an organism.

Ultraviolet irradiation is used for sterilizing laboratory equipment and reagents, disinfecting surfaces and materials, wastewater treatment, air disinfection, and for disinfection of various home devices from toothbrushes to tablet computers. There is an increasing demand in laboratories for methods that ensure the purity of DNA samples used as templates and reagents employed, especially for large-scale, automated genome analyses (e.g., high throughput amplification and sequencing methods). Reagents may include nucleic acids from contaminating microorganisms, human DNA introduced as a contaminant (while handling the reagents), microorganisms as contaminants which release their DNA when inactivated, and/or enzymes that exhibit activity even in the absence of nucleic acids or live microorganisms (e.g., an RNA library preparation for sequencing is an example). For example, touch contamination from human skin may include enzymes as well as microorganisms and shed human cells. Such contaminants, even if present in trace amounts, may interfere with nucleic acid amplification and affect the fidelity of sequencing. Thus, during the preparation of reagents for sequencing (e.g., for DNA sequencing using microfluidic technologies), sterilization of the reagents to free the reagents of unwanted contaminants (i.e. nucleic acids, various proteins, and microorganisms) may help eliminate false positive results, increase the signal-to-noise ratio, and generate reproducible and accurate high-throughput sequencing data. Cartridges used in preparation for DNA library sequencing, which are often contaminated through different sources, may be rendered contaminant-free by exposure to UV.

However, more resistant organisms may survive the single wavelength germicidal UVC exposure and multiply. Some organisms may even reactivate over time following UV inactivation, rendering the exposure ineffective. Further, the UV illumination of such large DNA sequencing chambers using gas-discharge lamp systems may not be uniform, which can increase sterilization times, energy consumption, and operating costs. Moreover, any contaminating microorganisms present in the reagent mix or present on surfaces in contact with the reagent mix may be lysed by the high temperatures used during the sequencing protocols, and may contribute additionally to the contaminating nucleic acids. The partially inactivated contaminating nucleic acids in the reagents or presence of microorganisms on surfaces and materials (e.g., tubes, plasticware), may interfere detrimentally with laboratory protocols, including DNA and/or RNA sequencing and amplification.

Thus, according to embodiments disclosed herein, the exposure of biological contaminants to select multiple wavelengths of light may yield complete and effective bio-inactivation of reagents and surfaces alike. Further, a multi-wavelength targeted approach may irreversibly inactivate microorganisms and other contaminants such as enzymes, preventing the issue of reactivation of microorganisms over time when treated with UV light of a single wavelength.

Figures 2, 4:
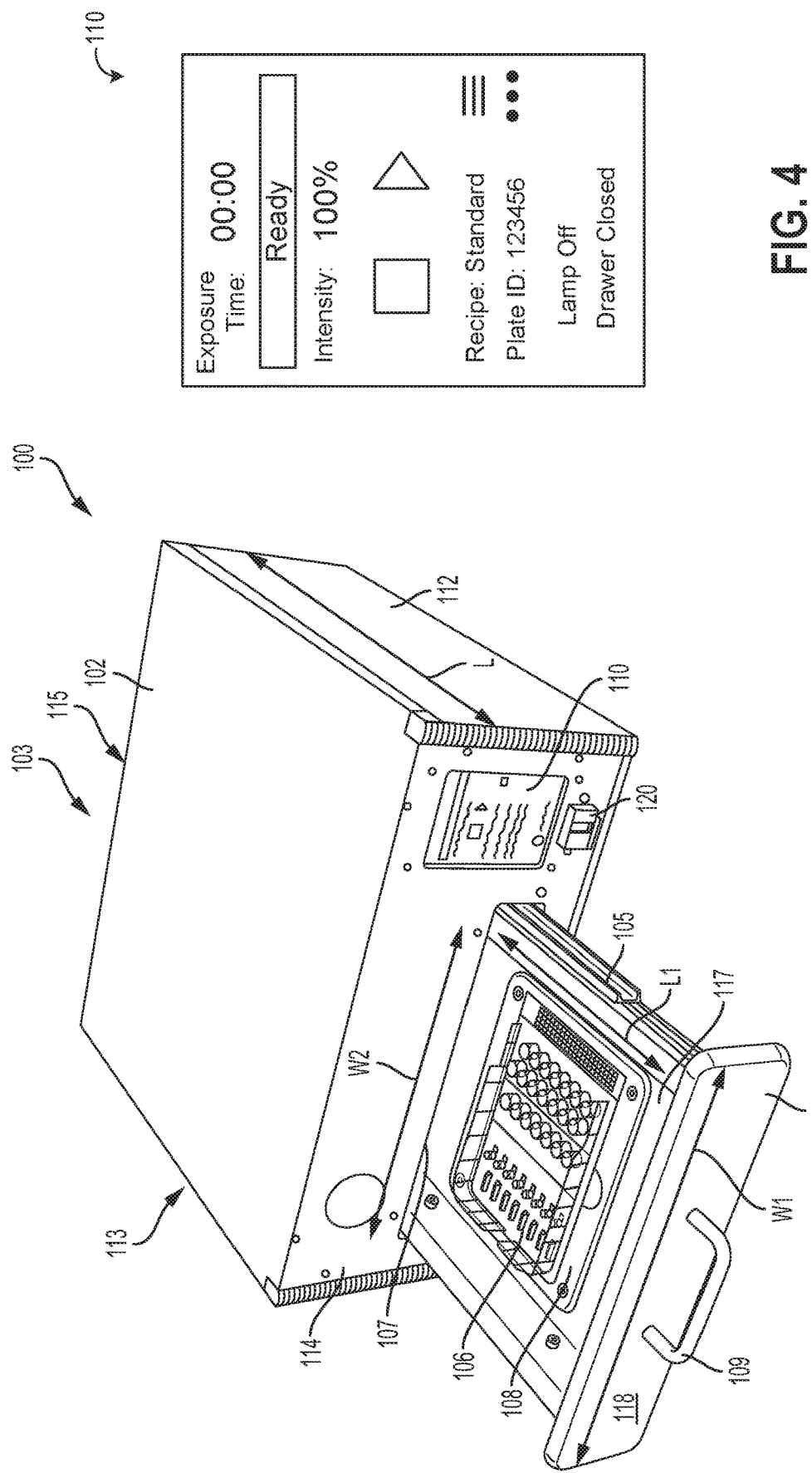
FIGS. 2-3 show the microplate irradiation system.
FIG. 4 shows a display screen of the microplate irradiation system.
Figure 3:
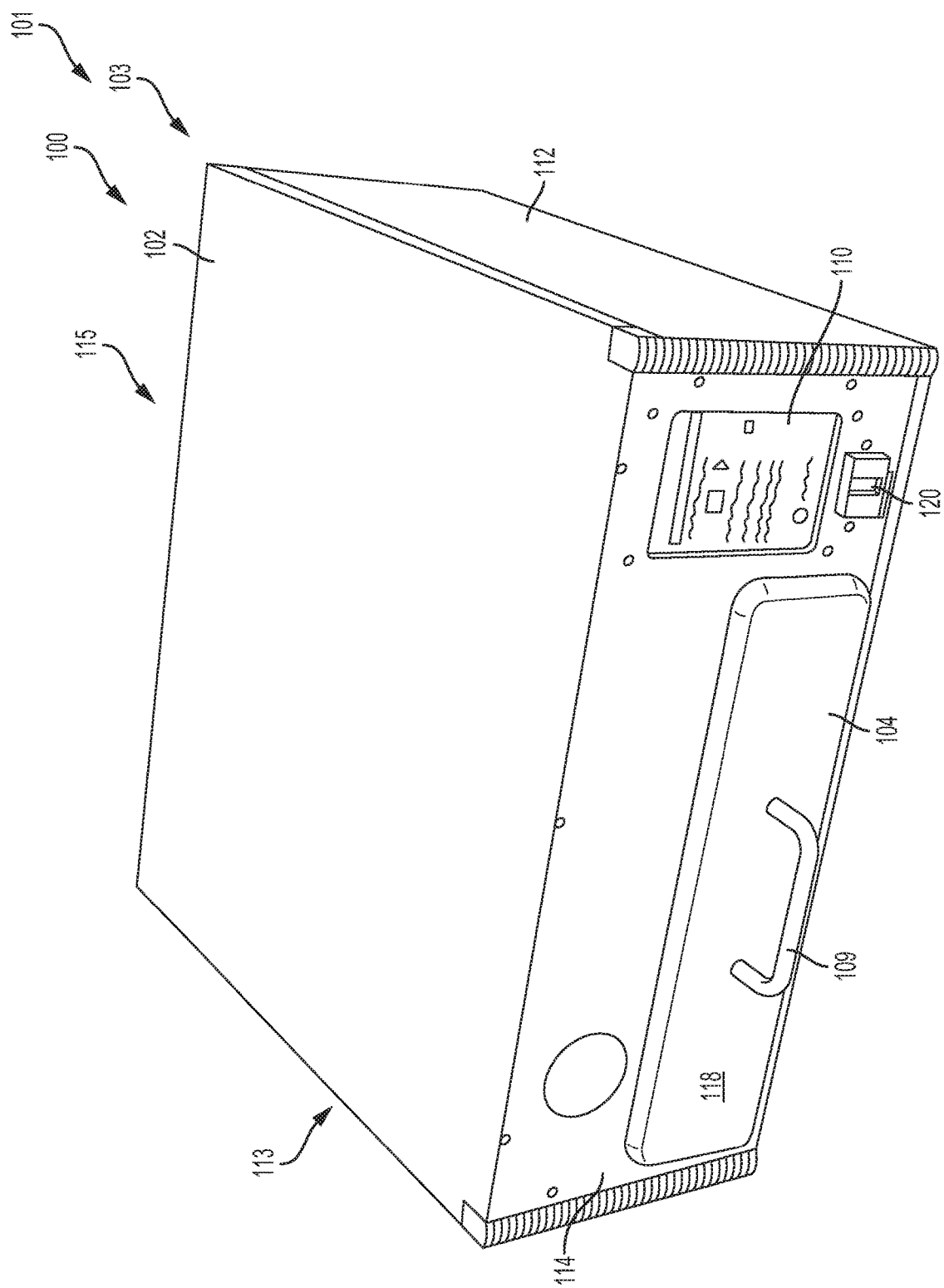
Figure 5:
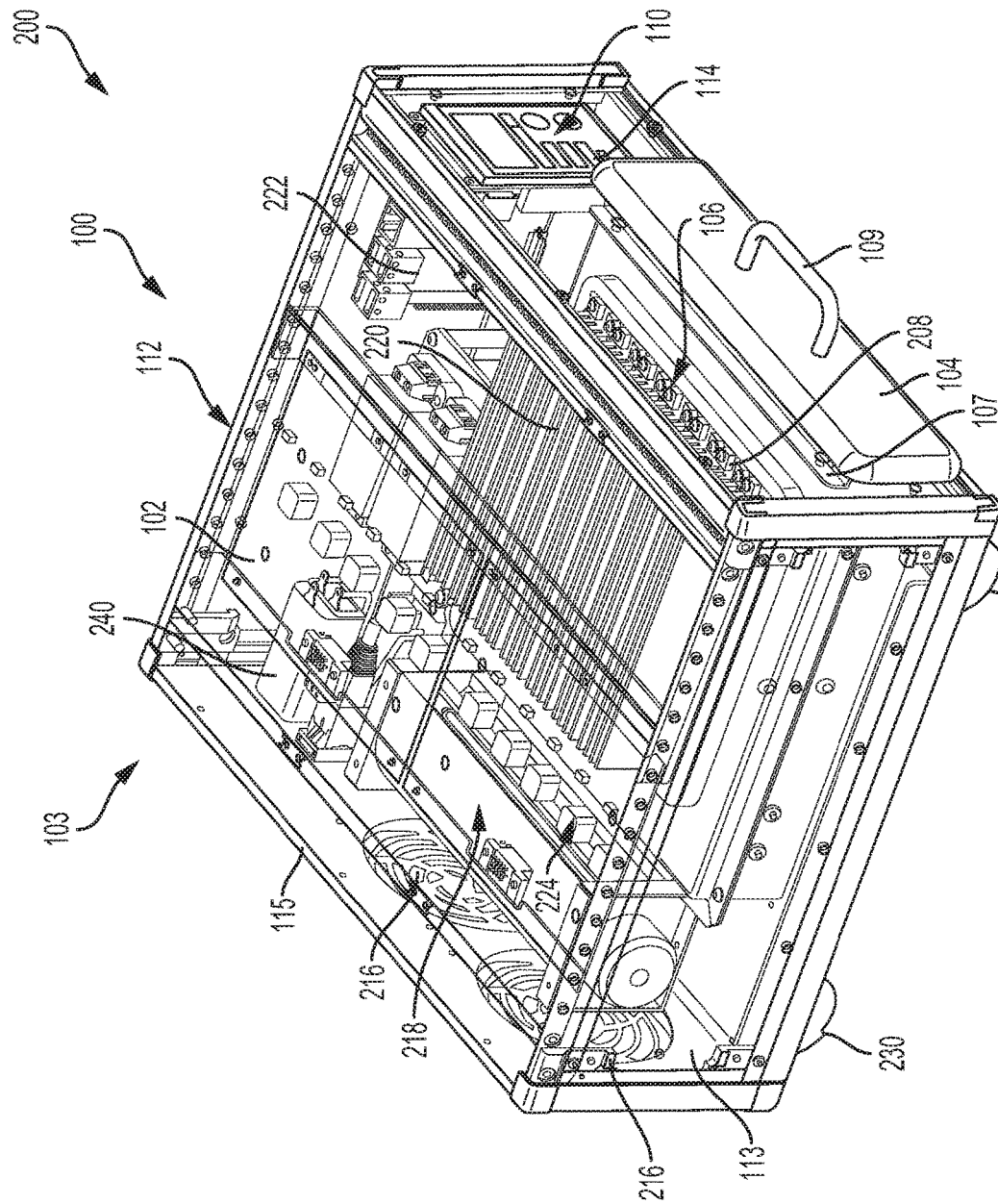
FIGS. 5-6 show transparent views of the microplate irradiation system.
Figure 6:
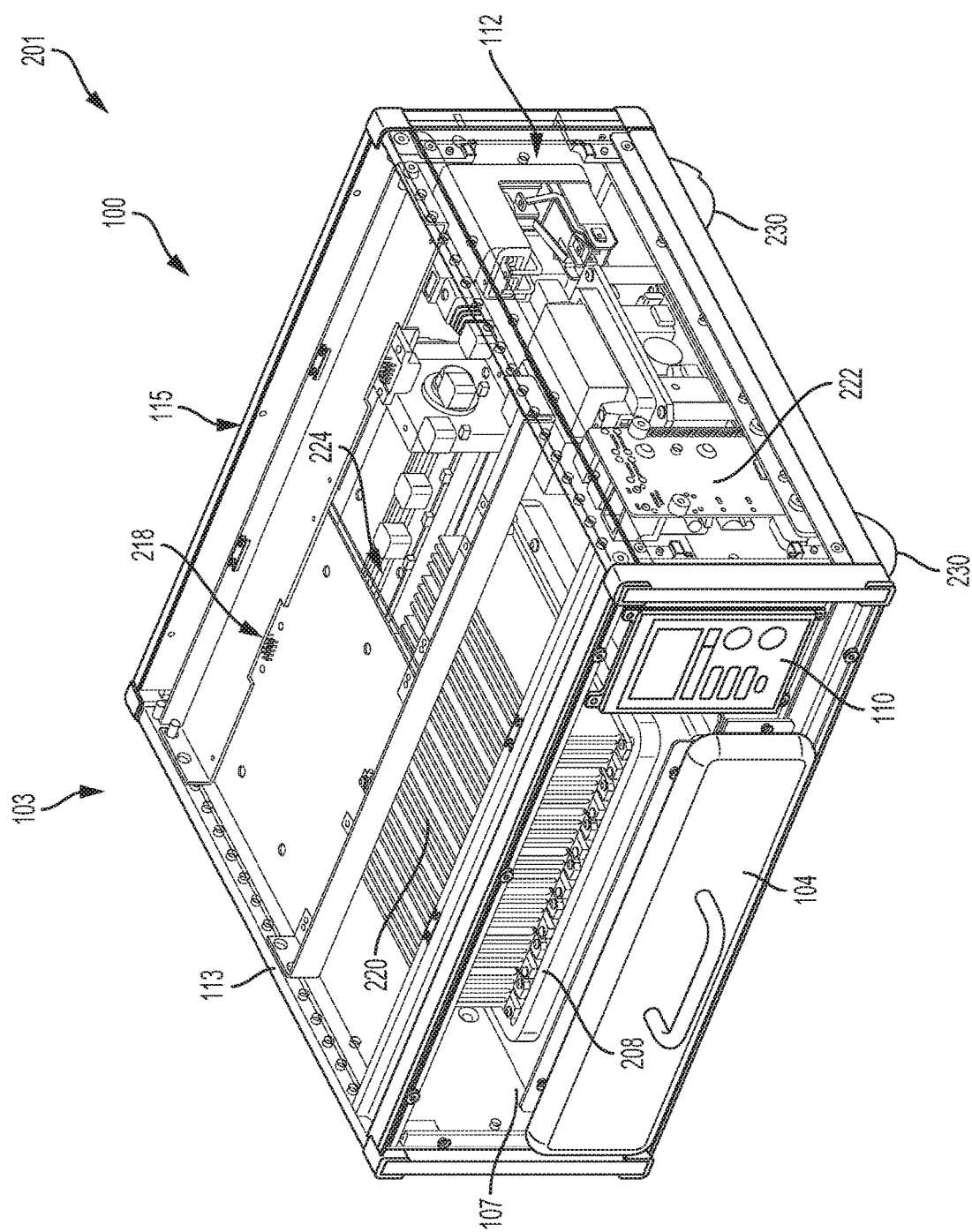
Figure 7:
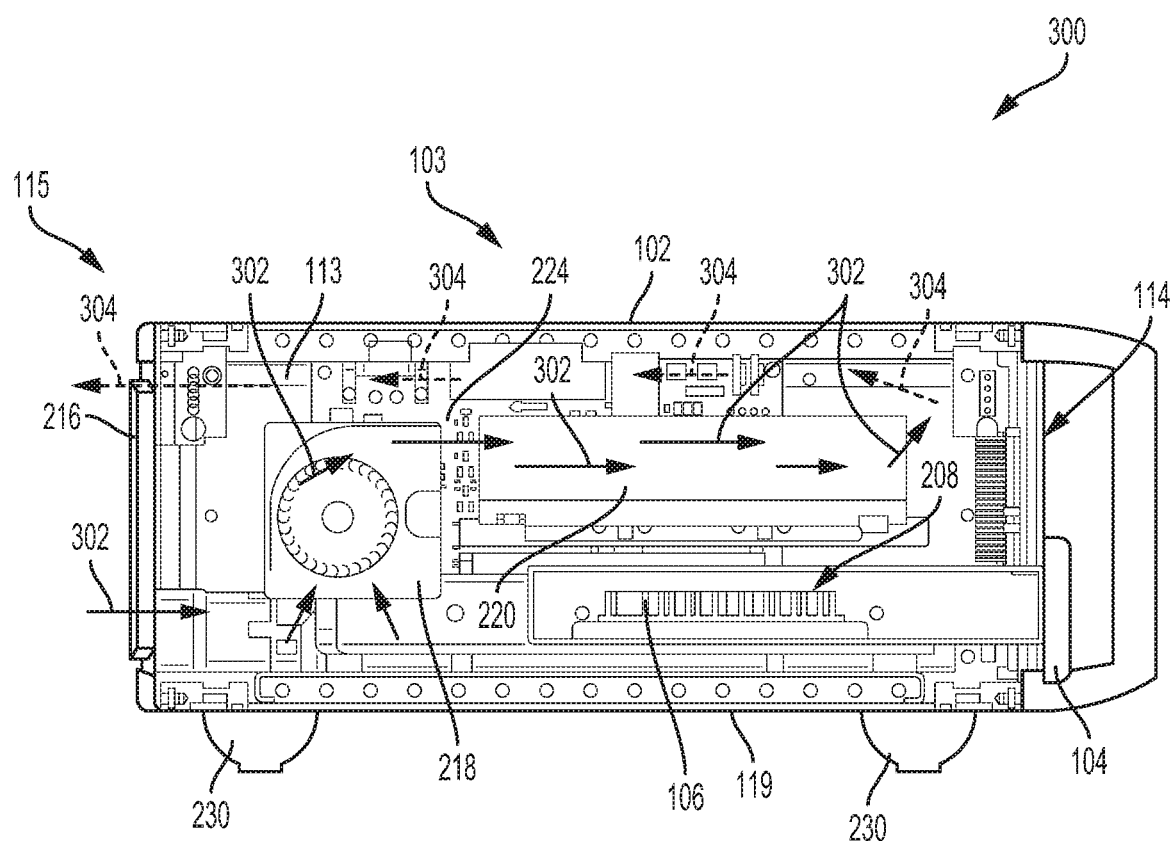
FIG. 7 shows air circulation through the microplate irradiation system.

FIG. 1 illustrates a schematic of a first embodiment of a bio-inactivation unit in the form of a microplate irradiation system. A microplate may be inserted within a chamber of the bio-inactivation unit, which includes the modular light-emitting engine, as shown in FIGS. 2-3. The microplate may be irradiated by activating the modular light-emitting engine through a menu on a display screen as shown in FIG. 4, where the display screen is coupled to a controller. FIGS. 5-6 illustrate the configuration of various components inside the microplate housing. The modular light emitting engine may be coupled to a controller and to a power supply and may be cooled by a venting mechanism as illustrated in FIG. 7. The modular light emitting engine may include a plurality of light emitting devices, wherein each device may include an array of light emitting diodes emitting germicidal radiation (e.g., UV-C), as illustrated in FIGS. 8-11. A duration, intensity, and pattern of irradiation may be regulated by the controller, to sterilize reagents contained in the microplate inserted into the bio-inactivation device via the method illustrated in FIG. 12.

Figure 13:
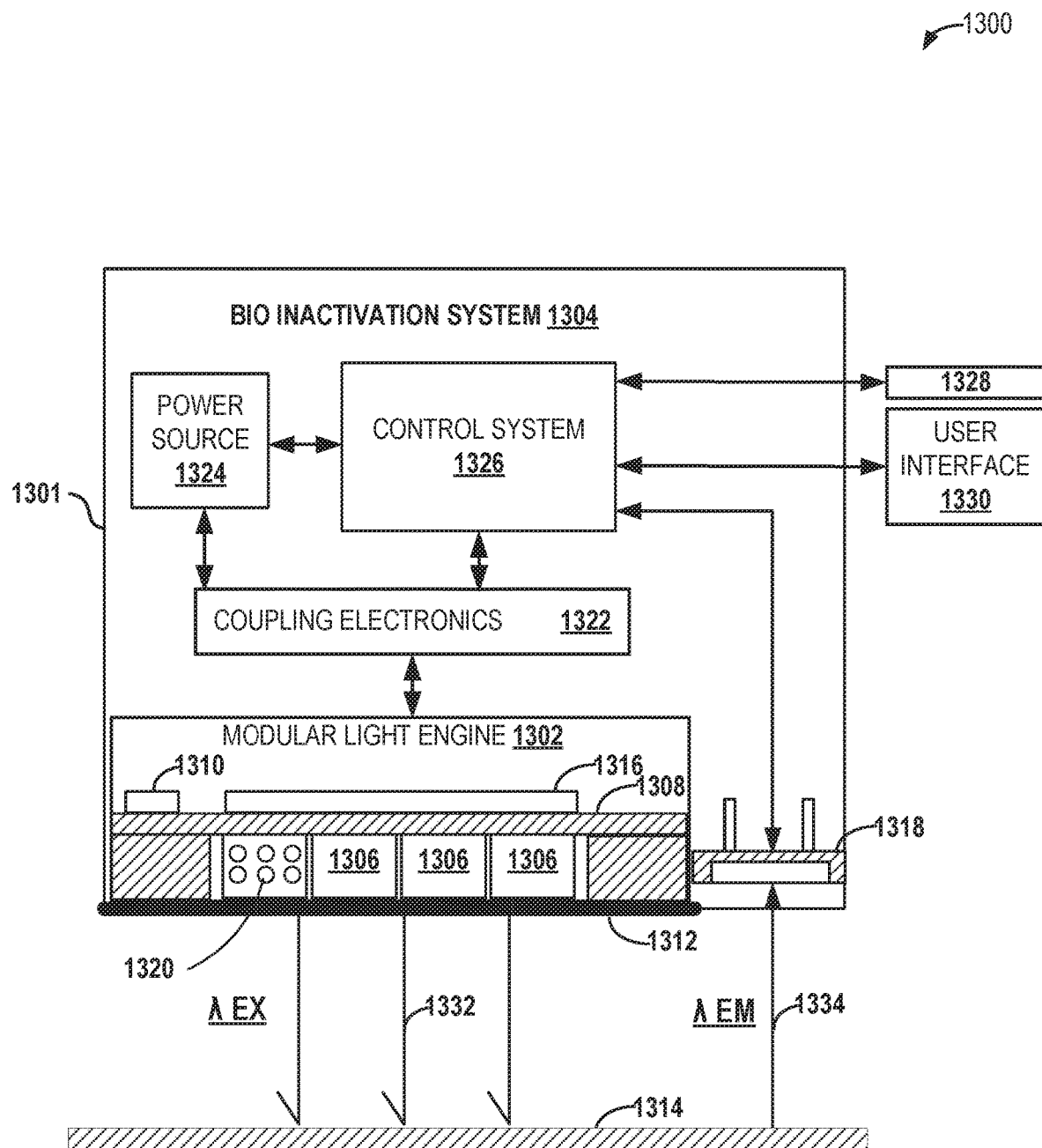
FIG. 13 illustrates a schematic of a second embodiment of a bio-inactivation device.
Figure 15:
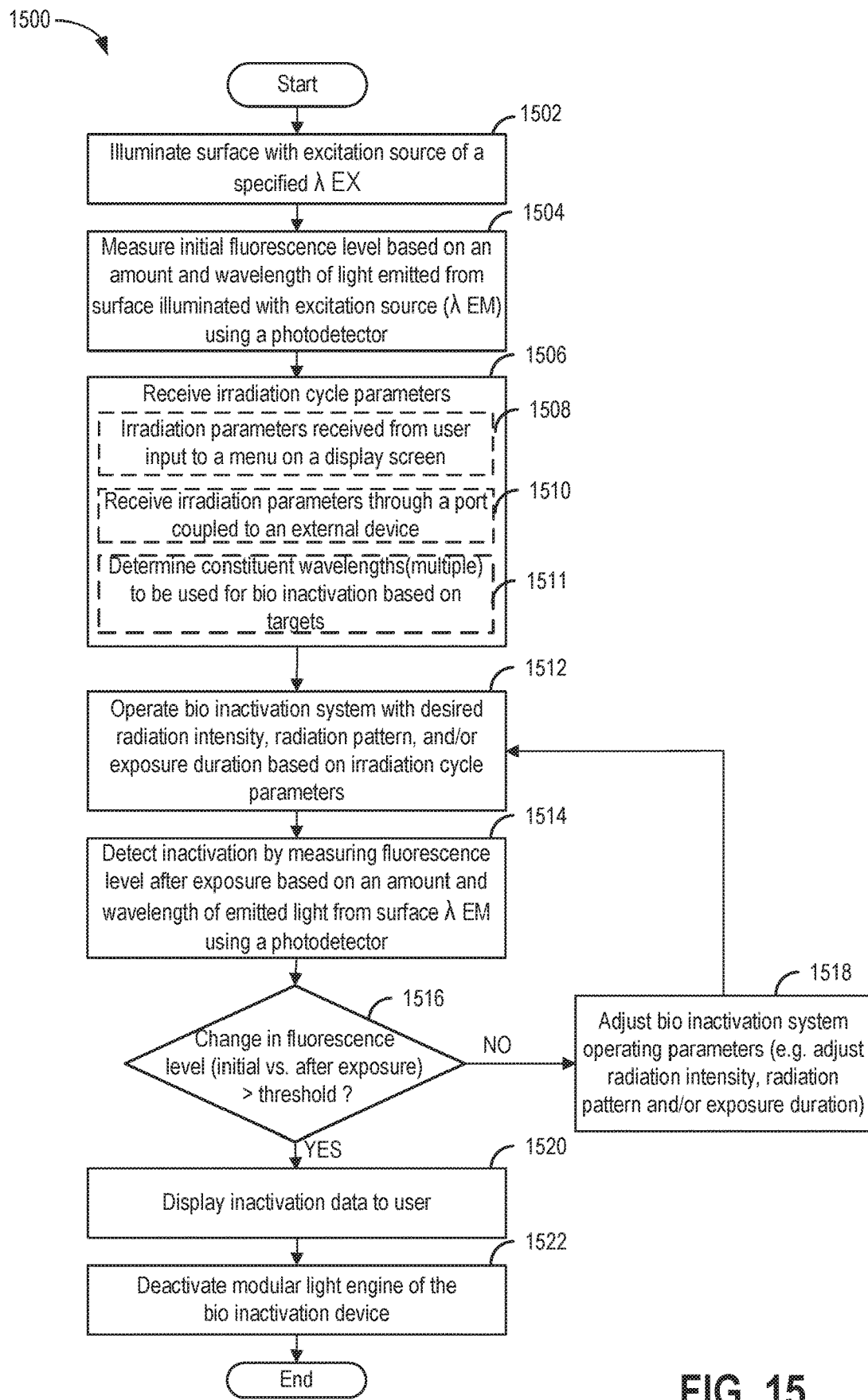
FIG. 15 illustrates a fluorescence-based method for determining bio-inactivation level using multi-wavelength germicidal light

In a second embodiment, a bio-inactivation device may be configured as a compact hand-held unit and may be used for the disinfection of surfaces and materials. The hand-held bio-inactivation device may be coupled to a photodetector which may determine a level of inactivation achieved based on emitted fluorescence as depicted in FIG. 13. Fluorescence levels may be measured prior to and after treatment of the surface with germicidal light. The emitted fluorescence from the treated surface may be compared to a threshold value and a level of inactivation may then be assessed as illustrated by the method of FIG. 15.

Figure 14:
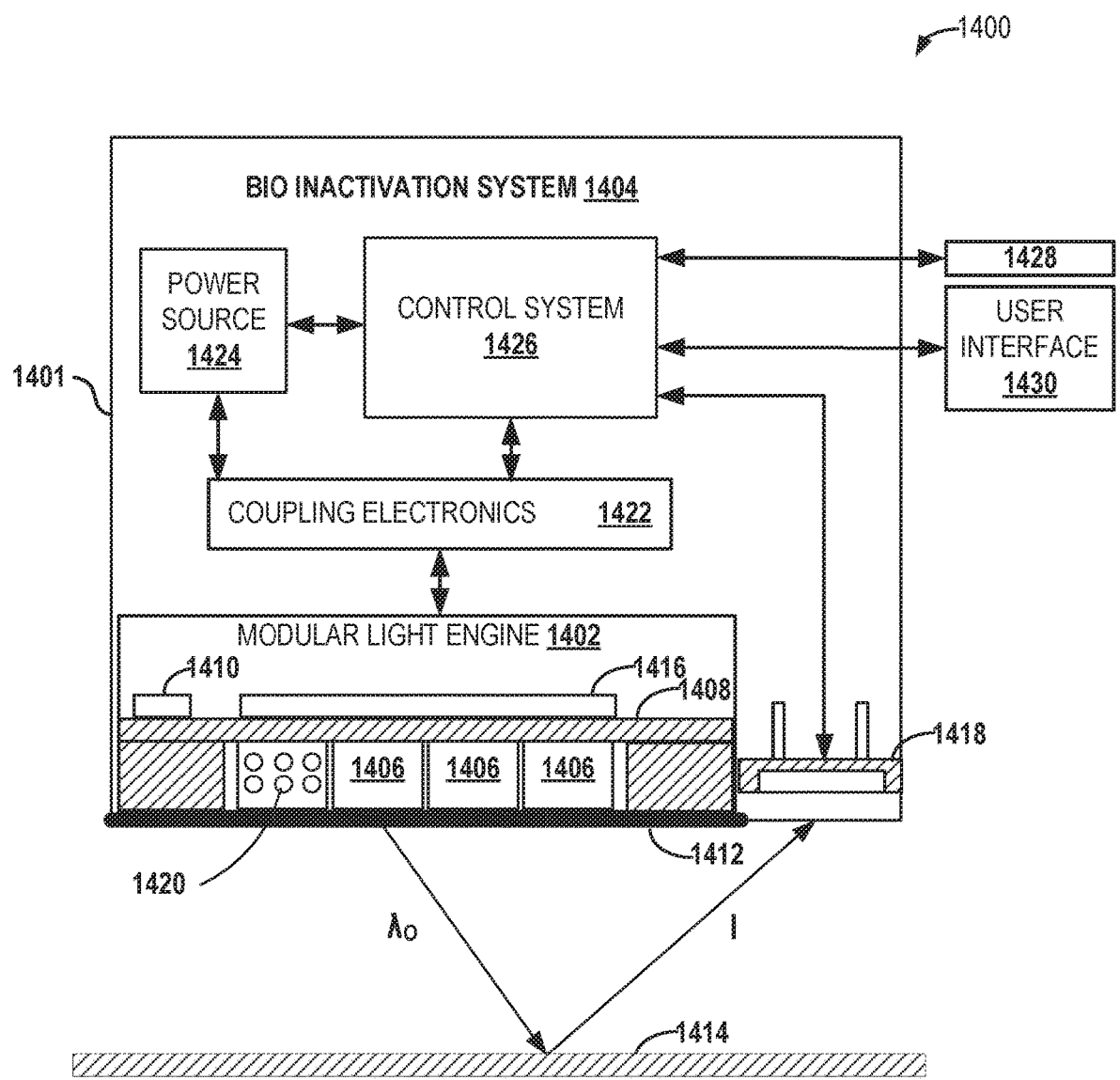
FIG. 14 illustrates a schematic of a third embodiment of a bio-inactivation device.
Figure 16:
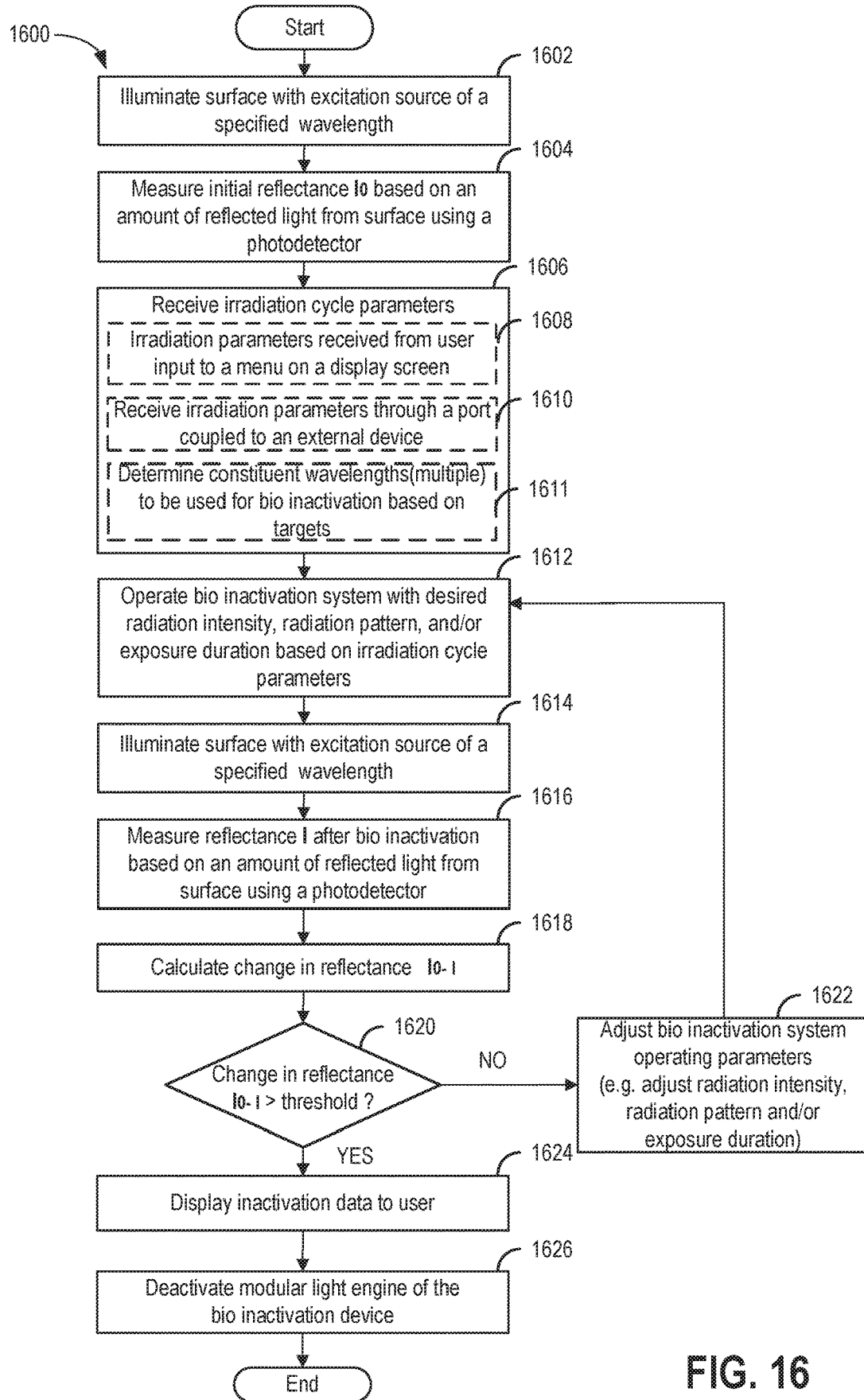
FIG. 16 illustrates a reflectance-based method for determining bio-inactivation level using multi-wavelength germicidal light.

In a third embodiment, a bio-inactivation device may be a hand-held unit for surface disinfection and may further be coupled to a photodetector. Herein, the photodetector may determine a level of inactivation achieved based on a change in reflectance from the untreated vs. the germicidal light treated surface as shown by the depiction of FIG. 14. The change in reflectance may be evaluated against a threshold and a degree of inactivation may be assessed as illustrated by the method of FIG. 16.

Figure 17:
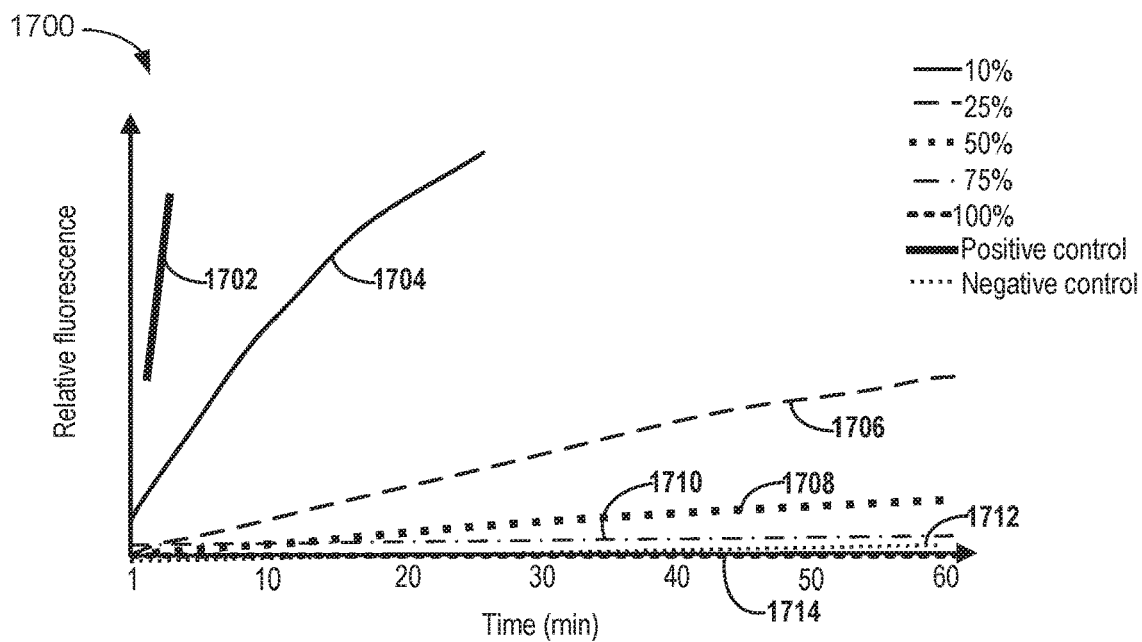
FIG. 17 shows a graph depicting RNase A enzyme activity at varied irradiance levels.
Figure 18:
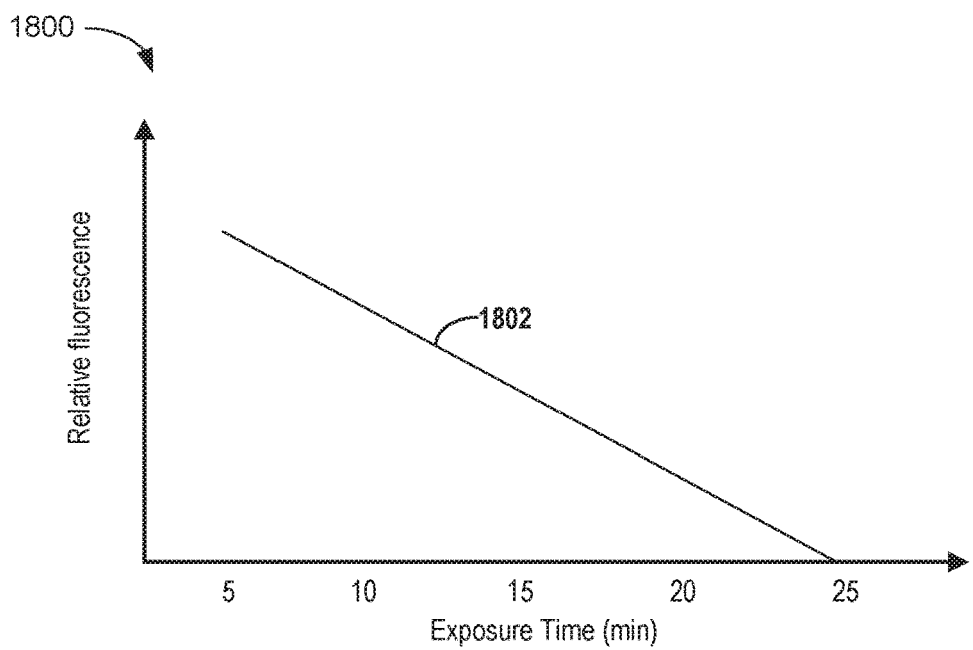
FIG. 18 shows a graph depicting RNase A enzyme activity with increasing exposure to 275 nm UV light at 50% relative irradiance level.

In order to assess the viability of the bio-inactivation device for effective disinfection of surfaces, a commonly found and easily measurable contaminant of the surface may be tested for inactivation. An example of a ubiquitous molecular contaminant present in living cells and frequently found on surfaces in the laboratory includes the ribonuclease enzyme protein RNase A. RNase A is highly resistant to denaturation (disruption of protein) and thus serves as an optimal target for the bio-inactivation device. FIG. 17 shows RNase A enzyme activity measured as relative fluorescence, when the surface containing RNase A is treated with UV light of 275 nm wavelength at various intensities (irradiance) for a specific duration. FIG. 18 shows RNase A enzyme activity when the surface with RNase A is treated with UV light of 275 nm wavelength at 50% irradiance over increasing durations of exposure to UV.

Figure 19:
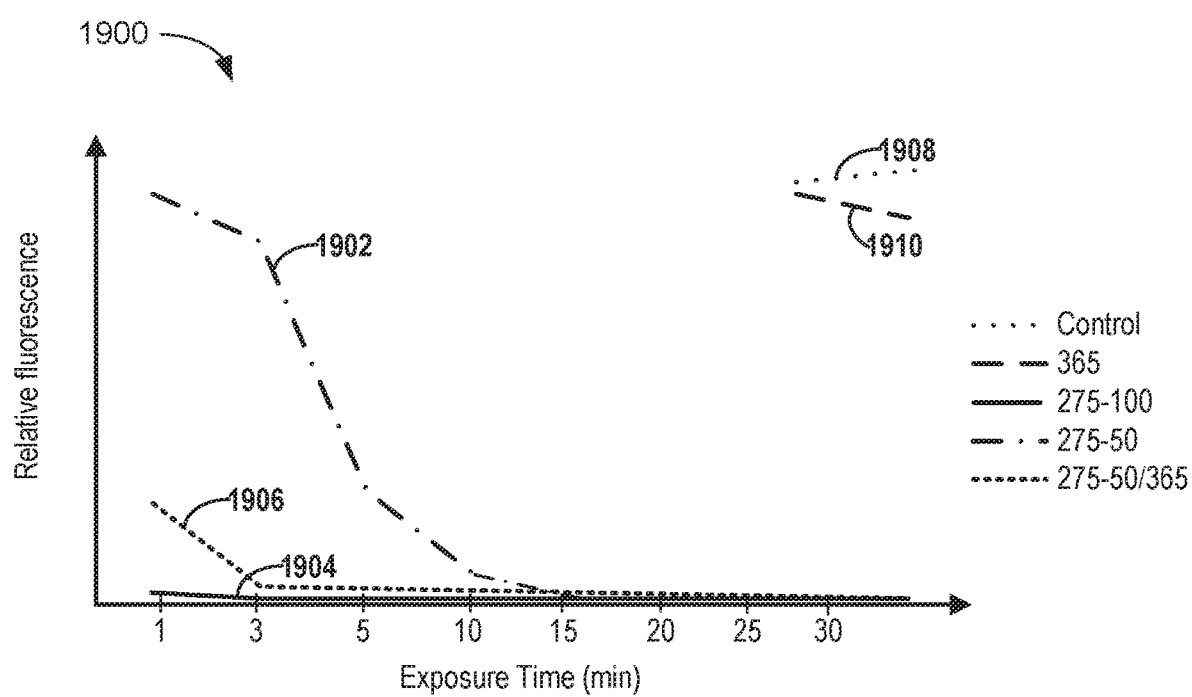
FIG. 19 shows a graph depicting the synergistic effect of using multiple UV light wavelengths on RNase A enzyme activity.

Most inactivation methods and systems employ a single wavelength of UV light optimal for inactivation of specific targets. However, by employing two or more wavelengths of light targeting different structures or pathways within organisms, a synergistic effect may be observed leading to a complete and efficient inactivation as depicted by FIG. 19. Regarding FIGS. 2-11, parts and features introduced once in description with reference to a figure may not be reintroduced and/or re-described with reference to subsequent figures and may be referred to by the same number.

Referring now to FIG. 1, a block diagram for an example configuration of a bio-inactivation device in the form of a microplate irradiation system 10 is illustrated. The microplate irradiation system 10 may be used to emit light, such as visible light, UV light, infrared light, and/or other types of radiation. In one example, microplate irradiation system 10 may comprise a modular light engine 12, a controller 14, and a power source 16.

The modular light engine 12 may include a plurality of semiconductor devices 19, as illustrated in FIG. 1, however in other examples, the modular light engine may include a single semiconductor device. Each of the plurality of semiconductor devices 19 may include an array 20 of light emitting diodes (LEDs), for example. In other examples, each semiconductor device may be an organic LED (OLED), laser diode, plasma discharge, or other light source. In one example, the array 20 may be a two-dimensional array of light emitting diodes. Semiconductor devices 19 may provide radiant output 24. In one example, the radiant output 24 may be UV-C radiation. The radiant output 24 may be directed to a microplate 26 positioned inside a drawer 25 inserted into a housing 11 of the microplate irradiation system 10. Returned radiation 28 may be directed back to the modular light engine 12 from the microplate 26 (e.g., via reflection of the radiant output 24). Some of the radiation output 24 may be returned back from the microplate 26 while some of the returned radiation may be from structures not directly in-line with the plurality of semiconductor devices emitting the radiation. An intensity of the radiation may be relayed to the controller 14. Based on the intensity of the returned radiation relayed, the controller may regulate the intensity of the radiant output 24 of the plurality of semiconductor devices 19.

The radiant output 24 may be directed to the microplate 26 via coupling optics 30. The coupling optics 30, if used, may be variously implemented. As an example, the coupling optics may include one or more layers, materials or other structures, such as flat windows, ball lenses, light guides, etc., interposed between the semiconductor devices 19 and the microplate 26, and providing radiant output 24 to surfaces of the microplate 26. The coupling optics 30 may be made from UV transparent materials such as fused silica, fused quartz, or other glass, silicone, polymers, or other materials.

Each of the layers, materials or other structure of coupling optics 30 may have a selected index of refraction. By selecting each index of refraction, reflection at interfaces between layers, materials, and other structures in the path of the radiant output 24 (and/or returned radiation 28) may be selectively controlled.

The plurality of semiconductor devices 19 may be coupled to the controller 14 via coupling electronics 22. The controller 14 may also be implemented to control the semiconductor devices, e.g., via the coupling electronics 22. The controller 14 may be connected to the power source 16 and may be implemented to modulate power supplied from the power source 16. Moreover, the controller 14 may receive data from the power source 16. In one example, the irradiance at one or more locations at the microplate 26 surface may be detected by sensors (for example, sensors along the surface of the microplate 26, adjacent to the surface of the microplate 26, and/or via returned irradiance 28) and transmitted to controller 14 in a feedback control scheme.

In addition to the power source 16 and the modular light engine 12, the controller 14 may also be connected to user interface 23. The user interface 23 may include a keyboard, mouse, display, and/or a touch screen display with a programmable menu, the programmable menu including duration of irradiation, intensity and dose of irradiation, and pattern of irradiation (that is, which of the semiconductor devices of the plurality of semiconductor devices will be operated at a given time). The controller 14 may also communicate to an external device 34 through one or more ports of the microplate irradiation system, such as USB port, LAN port, etc. The data received by the controller 14 from the user interface and/or the external device may be stored in a memory of the controller 14 and may be used to perform a programmed irradiation cycle.

The controller 14 may receive data of various types from one or more of the power source 16, the modular light engine 12, the external device 34, and/or the user interface 23. As an example, the data may be representative of one or more characteristics associated with coupled semiconductor devices 19. As another example, the data may be representative of one or more characteristics associated with the respective modular light engine 12, power source 16, user interface 23, and/or external device providing the data. As still another example, the data may be representative of one or more characteristics associated with the microplate 26 (e.g., representative of the radiant output energy or spectral component(s) directed to the microplate). Moreover, the data may be representative of some combination of these characteristics.

The controller 14, in receipt of any such data, may be implemented to respond to that data. For example, responsive to such data from any such component, the controller 14 may be implemented to control one or more of the power source 16, the modular light engine 12 (including one or more such coupled semiconductor devices), etc.

Individual semiconductor devices 19 (e.g., LED devices) of the modular light engine 12 may be controlled independently by controller 14. For example, controller 14 may control a first group of one or more individual LED devices to emit light of a first intensity, wavelength, and the like, while controlling a second group of one or more individual LED devices to emit light of a different intensity, wavelength, and the like. The first group of one or more individual LED devices may be within the same array 20 of semiconductor devices, or may be from more than one array of semiconductor devices. Array 20 may also be controlled independently by controller 14 from other arrays of the modular light engine. For example, the semiconductor devices of a first array may be controlled to emit light of a first intensity, wavelength, and the like, while those of a second array in the modular light engine may be controlled to emit light of a second intensity, wavelength, and the like. Further, in some examples, a first subset of semiconductor devices of array 20 may be controlled to emit light of a first intensity and first wavelength, while a second subset of semiconductor devices of array 20 may be controlled to emit light of a second intensity and/or second wavelength.

As described above, the microplate irradiation system 10 may be configured to receive the microplate 26 placed in the drawer 25 that may be inserted inside housing 11 below the modular light engine. The microplate irradiation system 10 may also include a safety interlock system to activate and deactivate the modular light engine 12 if the chamber is closed and opened, respectively.

FIGS. 2 and 3 show a microplate irradiation system 100 (similar to the microplate irradiation system 10 of FIG. 1), including a housing 103. The housing 103 includes a front face 114, perpendicular to a top surface 102 and a bottom surface 119 of the housing 103. A back face 115 of the housing is opposite to the front face 114, and is perpendicular to the top surface 102 and the bottom surface 119. The front face 114 includes a drawer 104 that slides into and out of an opening 107 of the front face 114. The housing 103 also includes a first side surface 112 and a second side surface 113, opposite and parallel to the first side surface 112. Each of the first side surface 112 and second side surface 113 may be perpendicular to the top surface 102 and bottom surface 119 along a length L of the first side surface and the second side surface. The microplate irradiation system 100 may be a benchtop irradiation system and may be stackable.

The drawer 104 may be fully extended out of the opening 107 or may be inserted completely inside the opening 107, as shown in FIGS. 2 and 3, respectively. A length L1 of the drawer 104 may be less than the length L of the side surface, such that the drawer may fully insert into the opening 107. A mechanism 109 may be present on a drawer front 118 of the drawer 104 to pull the drawer out of the opening 107 or to push back the drawer into the opening 107. In one example, the drawer 104 may be inserted and extended out of the opening 107 using a switch (not shown), wherein the switch may be electrically operated.

A width W1 of a drawer front 118 may be more than a width W2 of the opening 107, such that a drawer front 118 of the drawer 104 is in face sharing contact with the front face 114 of the housing 103 around the opening 107 when the drawer is in a fully inserted position, as illustrated in FIG. 3.

The drawer 104 may include channels 105, which may slide into complementary grooves (not shown) inside the opening 107, thus enabling the drawer to slide in and out of the opening 107. In one example, when the drawer is in the fully extended position out of the opening, the drawer may not be detached from the housing 103. In another example, the drawer 104 may be reversibly detached from the housing 103. In a further example, a door (for example, a hinged door, a sliding door etc.) instead of the drawer may be configured to block and unblock the opening 107.

The drawer 104 includes a cavity 117 with a stage 108. The stage 108 may be configured to hold a reagent-holding device 106. In one example, the reagent-holding device 106 may be a multi-well microplate, for example, a 96 well plate or a 48 well plate. In another example, the reagent-holding device 106 may be one or more microfluidics chip devices and/or cartridges. Other examples of the reagent-holding device 106 may be a cuvette, a tissue culture flask, a slide, a tissue culture single well plate, etc. In a further example, the stage may be configured to hold more than one reagent holding device. The reagent-holding device 106 may be reversibly fixed to the stage 108 (e.g., using one or more clasps), such that sliding the drawer 104 in and out of the opening 107 may not dislodge the reagent-holding device 106 from the stage 108. Additionally, the stage 108 with the reagent-holding device 106 may not interfere with the drawer sliding in and out of the opening 107. In some examples, the reagent-holding device 106 may include a lid comprised of material that is UV-transparent, such as clear silicone, polytetrafluoroethylene (PTFE), or fluorinated ethylene propylene (FEP). In such examples, the reagent-holding device may be inserted into the cavity/drawer with the lid coupled to the base of the reagent-holding device. However, in examples where a lid of the reagent-holding device is not UV-transparent (e.g., lids comprised of polyester or polyimide), the lid may be removed prior to insertion into the cavity/drawer.

The front face 114 of the microplate irradiation system 100 also includes a display screen 110 adjacent to the drawer 104, as illustrated in FIGS. 2-3. A magnified version of the display screen 110 is also illustrated in FIG. 4. In one example, the display screen 110 may be a touch screen. The display screen 110 may include a menu to operate the microplate irradiation system 100. The display menu may be coupled to a controller (for example, the controller 14 of FIG. 1), which may regulate operation of a light source (such as time of light source activation, intensity of the light source, etc.) as will be discussed further below. In other examples, the display screen may be positioned along the top surface, or may be positioned along a first side surface or a second surface of the housing 103.

As shown in FIG. 4, the display screen may include user interface control elements that allow a user to input various parameters and/or commands. For example, a user may select sterilization protocol (also referred to as a recipe), which defines the light output parameters (e.g., power or irradiance level, emission pattern, temporal duration, wavelength spectrum). The user may also initiate activation and termination of the sterilization procedure. The display screen may also display information regarding the sterilization procedure to the user, including exposure time, intensity level, selected recipe, microplate identification, light emitter status, and drawer status.

A port 120 may be present along the front face 114 of the microplate irradiation system 100. In one example, the port 120 and/or additional ports may be present along other surfaces of the housing, such as along the first side surface and/or the second side surface or at the back face. The port 120 may be a wired and/or wireless communication means, such as a USB connection, a wireless internet connection, an infrared transponder, or a Bluetooth® link. The microplate irradiation system 100 may be connected through the port 120 directly and/or indirectly (via the internet, an intranet, cellular network, PSTN or any other network) to an external CPU, such as a computer, having appropriate software to select or configure one or more irradiation parameters and transfer them to a memory of a controller of the microplate irradiation system 100. Alternatively, the external device could be a memory store such as a ROM, e.g., a USB stick, on which one or more light irradiation parameters are stored, which are transferred to the microplate irradiation system 100 controller memory upon connection.

FIGS. 5 and 6 show a first transparent view 200 and a second transparent view 201 respectively of the microplate irradiation system 100 described above with reference to FIGS. 2-3. The first transparent view 200 and the second transparent view 201 illustrate the configuration of components inside the housing 103 of the microplate irradiation system 100. Parts and features introduced previously in FIGS. 2-3 are not reintroduced and are referred to by the same number.

FIGS. 5 and 6 show transparent views of housing 103 with base supports 230 along the bottom surface 119 of the microplate irradiation system. The reagent-holding device 106, for example, a microplate with a liquid reagent, may be in the drawer inserted inside the opening 107. A modular light engine 220 may be positioned directly above the reagent-holding device 106, such that light emitted from the modular light engine 220 may be directed towards a top surface of the reagent-holding device 106.

The modular light engine 220 may be a non-limiting example of modular light engine 12 of FIG. 1 and thus include a plurality of light source devices (similar to the plurality of semiconductor devices 19 of FIG. 1) as will be described below with reference to FIGS. 7-11. The modular light engine 220 may be coupled to a controller 218 (similar to the controller 14 of FIG. 1) inside the housing 103 of the microplate irradiation system 100. The controller 218 may be coupled to a power source 240 (similar to the power source 16 of FIG. 1). In one example, the input power from the power source may be in the range of 90-260 VAC, 47-63 Hz. The controller 218 may also be coupled to the display screen 110 through coupling electronics 222 and may be coupled to the modular light engine 220 through coupling electronics 224. The controller may communicate with the display screen 110 and with the port 120, as described above with reference to FIG. 2.

Air vents 216 may be present along the back face 115 of the housing 103. The vents 216 enable the circulation of air through the housing 103 to reduce the temperature increase during operation of modular light engine 220 inside the housing 103. In one example, a fan (not shown) may be contained within the housing (e.g., adjacent to the vents 216), to further aid in air-circulation through the housing 103.

A transparent side view 300 illustrating air circulation through the housing 103 of the microplate irradiation system 100 is shown in FIG. 7. Air may enter the housing through the vent 216 along the back face of the housing 103. Cooler ambient air may flow through the vent 216 along an airflow path 302 towards the front face 114 of the housing, flowing past the controller 218, the coupling electronics 224, and the modular light engine 220. The air temperature increases as heat is transferred convectively while flowing past the controller, the electrical circuit, and the modular light engine. The heated air flows along a path 304 and exits the housing through the vent 216, thus reducing the internal temperature of the housing while operating the modular light engine.

Figure 8:
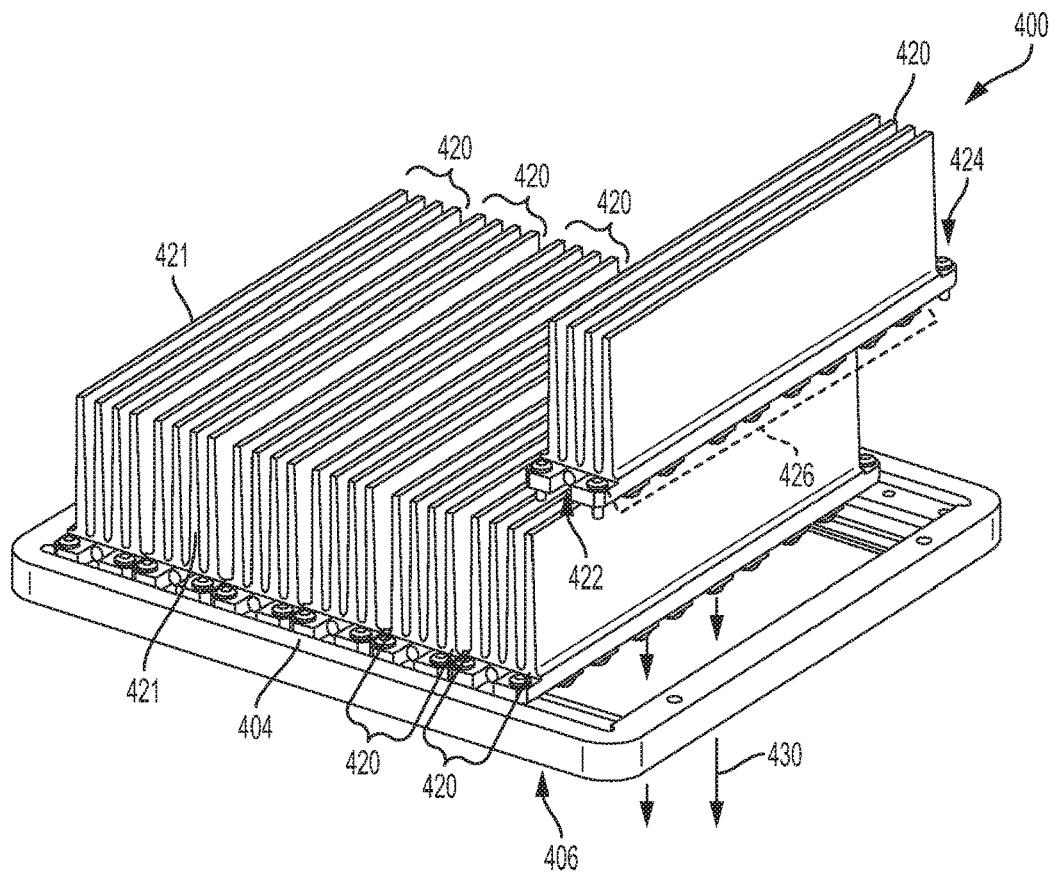
FIGS. 8-9 illustrate a modular light engine of the microplate sterilizing system.
Figure 9:
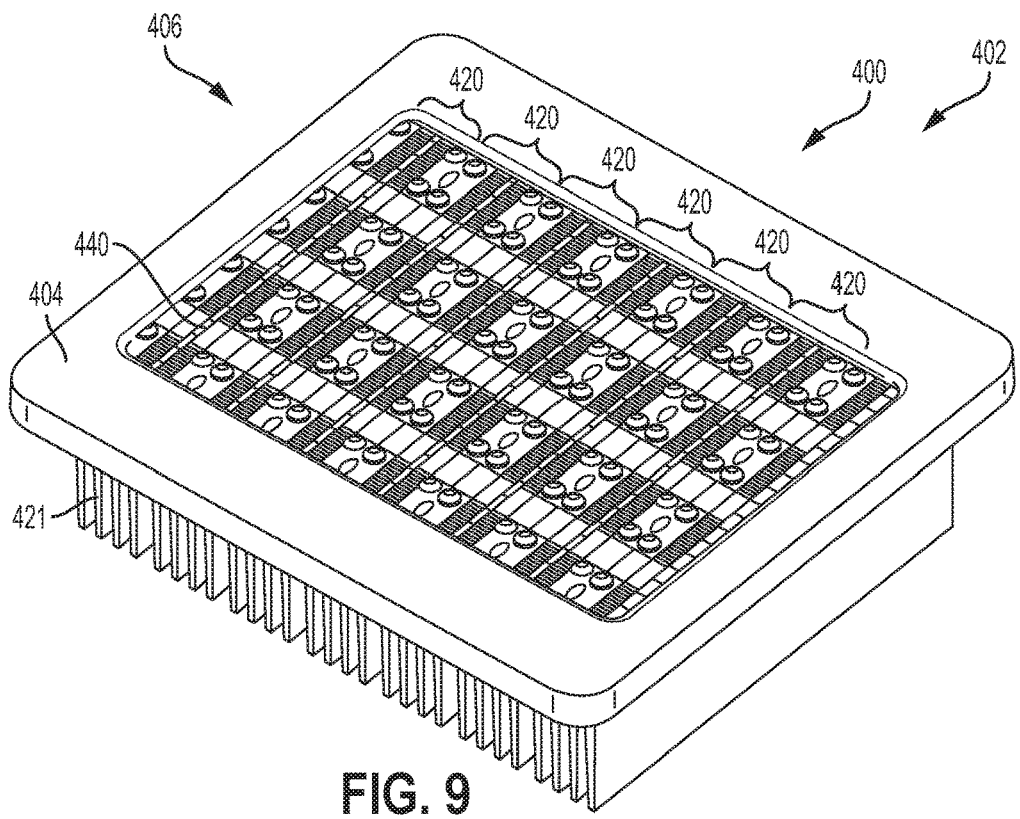

FIGS. 8-9 illustrate a modular light engine 400. Modular light engine 400 is one non-limiting example of modular light engine 220 of FIGS. 2-3 and 5-6 and modular light engine 12 of FIG. 1. The modular light engine 400 may include a plurality of light emitting devices 420. In the illustrated example, each light emitting device 420 may include an array of LEDs arranged on a heatsink. In another example, the plurality of light emitting devices 420 may be one or more tiles and/or strips, where each tile and/or strip may include a two-dimensional array of LEDs emitting radiation.

Each light emitting device 420 comprises an array of LEDs coupled to a substrate. Each substrate is coupled to a heatsink, herein a set of cooling fins. Each light emitting device 420 substrate forms the front surface of the light emitting device (e.g., light-emitting surface) and may include a first end 422 and a second end 424 (opposite the first end 422). The first end 422 and the second end 424 of each of the light emitting device substrates may be in contact with the frame 404, while a center section 426 (e.g., face) of each of the light emitting devices faces a reagent-holding device (e.g., device 106 of FIGS. 5-6). Light is emitted from each of the light emitting devices 420 unobstructed towards the reagent-holding device. The direction of light emitted from the light emitting device is indicated by arrows 430. In one example, the frame 404 may be configured to accommodate up to seven light emitting devices, as illustrated in FIG. 8. In other examples, the frame 404 may be configured to accommodate more than seven or less than seven light emitting devices. Fins 221 along a rear surface of each of the light emitting devices 420 face away from the reagent-holding device and may enable air circulation to reduce overheating of the modular light engine.

In one example, the frame 404 may be directly above and correspond to the stage 108 with the reagent-holding device (without being in face-sharing contact with the reagent-holding device) when the drawer 104 is fully inserted in the opening 107, as illustrated in FIGS. 3 and 5-6. The light emitted by the light emitting devices 420 may be directed to the top surface 208 of the reagent-holding device 106.

FIG. 9 shows a view 402 of a front surface 406 of the light emitting devices 420. Each of the light emitting devices 420 includes a row of LEDs 440 (while seven rows of LEDs are shown in FIG. 9, only one row is labelled in FIG. 9). The LEDs may emit UV, IR, and/or visible light. The UV light wavelength may be in the range of 100 nm-290 nm (for example, 275 nm), which is germicidal and can denature nucleic acids, including the contaminating nucleic acids present in the reagent inside the reagent-holding device. However, other wavelengths are possible, including multiple wavelengths, as described in more detail below.

Figure 10:
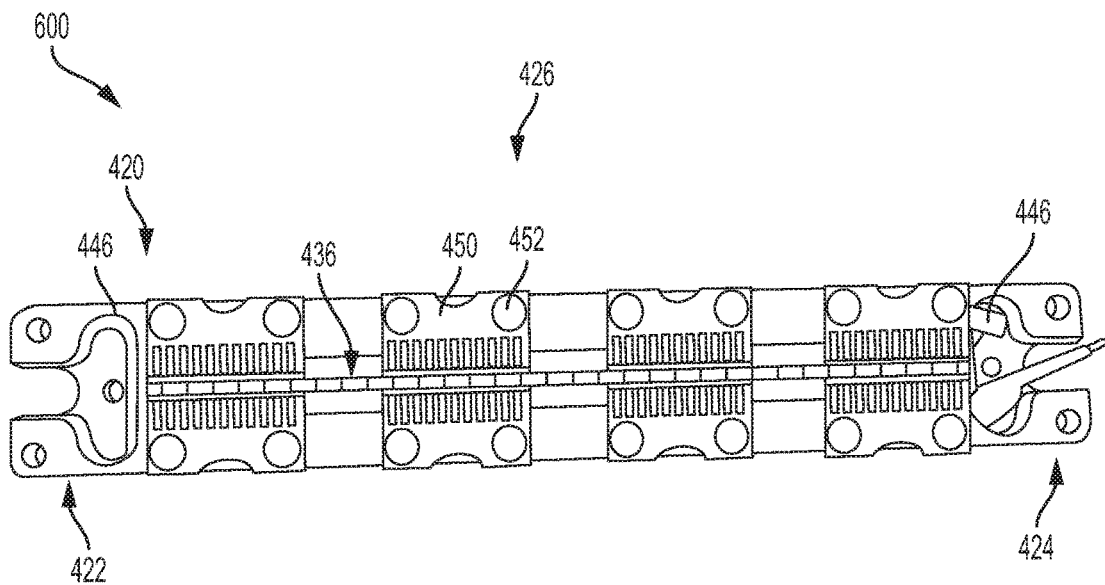
FIG. 10 illustrates a single light-emitting device of the modular light engine.

FIG. 10 shows a top view 600 of the light emitting device 420, with the first end 422 and the second end 424. Each of the first end and the second end includes a retaining mechanism 446, which is configured to couple each of the first end and the second end of the light emitting device 420 to the frame 404, as illustrated in FIGS. 8-9. The center section 426 of the light emitting device includes a row of LEDs 436. As shown in FIG. 10, the light emitting device 420 may include one row of LEDs, where the row can accommodate up to four groups of LEDs, with up to eight LEDs in each group. However, the actual number of LEDs included in the light emitting device may vary. In one example, the row of LEDs 436 may include eight LEDs spaced apart from each other uniformly or non-uniformly. In other examples, a different distribution of the LEDs in the center section 426 of the light emitting device may be seen, such as more or fewer LEDs, more than one row, etc. The light emitting device shown in FIG. 10 may have a width of 23 mm, although other widths are possible. Light emitting device 420 further includes a plurality of finger clips, such as clip 450, held down by screws, such as screw 452. The finger clips may establish electrical contact with the LEDs.

Each of the LEDs or groups of LEDs (i.e. rows, columns, or groups within the rows or columns), may be coupled to the controller and each LED or group of LEDs activated and deactivated by the controller. The controller may regulate the power supply to the LEDs based on input received from a user through the display screen 110 or through the port 120, as described above. Each of the LEDs may emit light of the same intensity, such that the reagent-holding device receives a uniform dose (for example, approximately 80% uniformity) of UV light on the top surface of the reagent-holding device facing the LEDs. In one example, UV light emitted by the modular light emitting engine may have an approximate intensity of 4.8 mW/cm$^2$ at the top surface of the reagent-holding device. The light generated is incident on the reagent-holding device, thus irradiating the reagent-holding device uniformly.

Each of the light emitting devices may be regulated individually by the controller. Similarly, the output of each of the LEDs or groups of LEDs may be regulated by the controller. In one example, only a first section of the reagent-holding device may be irradiated by activating only the light emitting devices corresponding to the first section. A second section of the reagent-holding device may receive no incident light emission by not activating the light emitting devices corresponding to the second section. In a further example, the light emitting devices corresponding to the first section of the reagent-holding device may be operated at a different intensity and/or a different temporal duration than the light emitting devices corresponding to the second section of the reagent-holding device.

Figure 11:
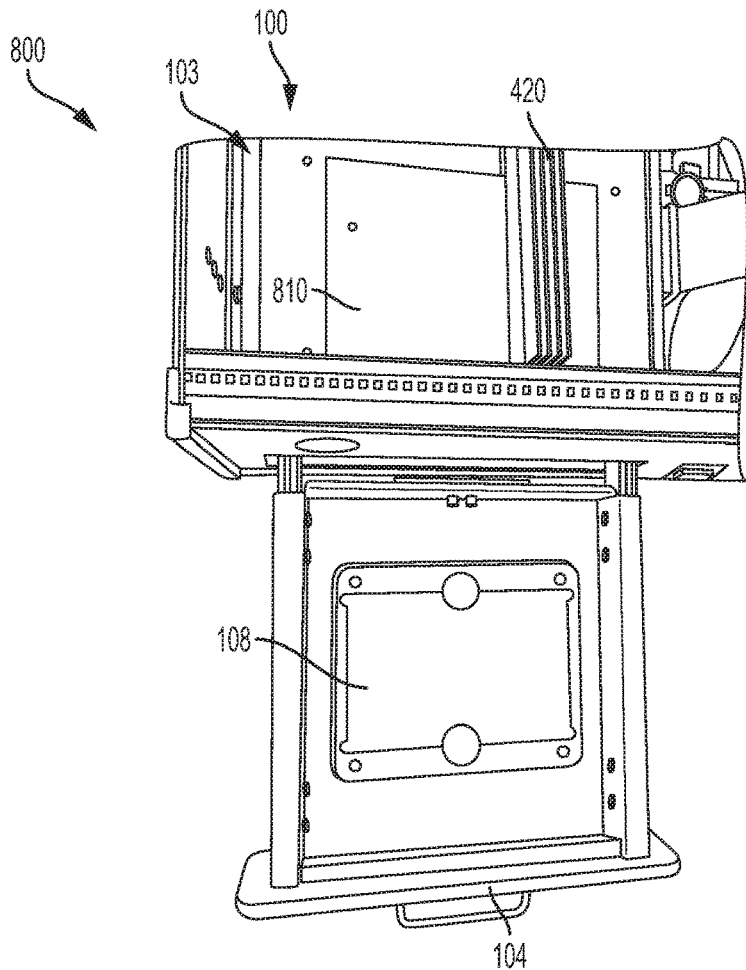
FIG. 11 illustrates a light-emitting device inside a housing of the microplate irradiation system.

FIG. 11 shows a view 800, where one light emitting device 420 is positioned inside the housing 103 of the microplate irradiation system 100. The light emitting device 420 is positioned over a cavity 810. The drawer 104 is extended outside the housing 103. The stage 108 is configured to receive a microplate. When the microplate is positioned on the stage and the drawer is inserted into the housing, the light emitting device 420 is positioned over the microplate for delivering germicidal irradiation.

Figure 12:
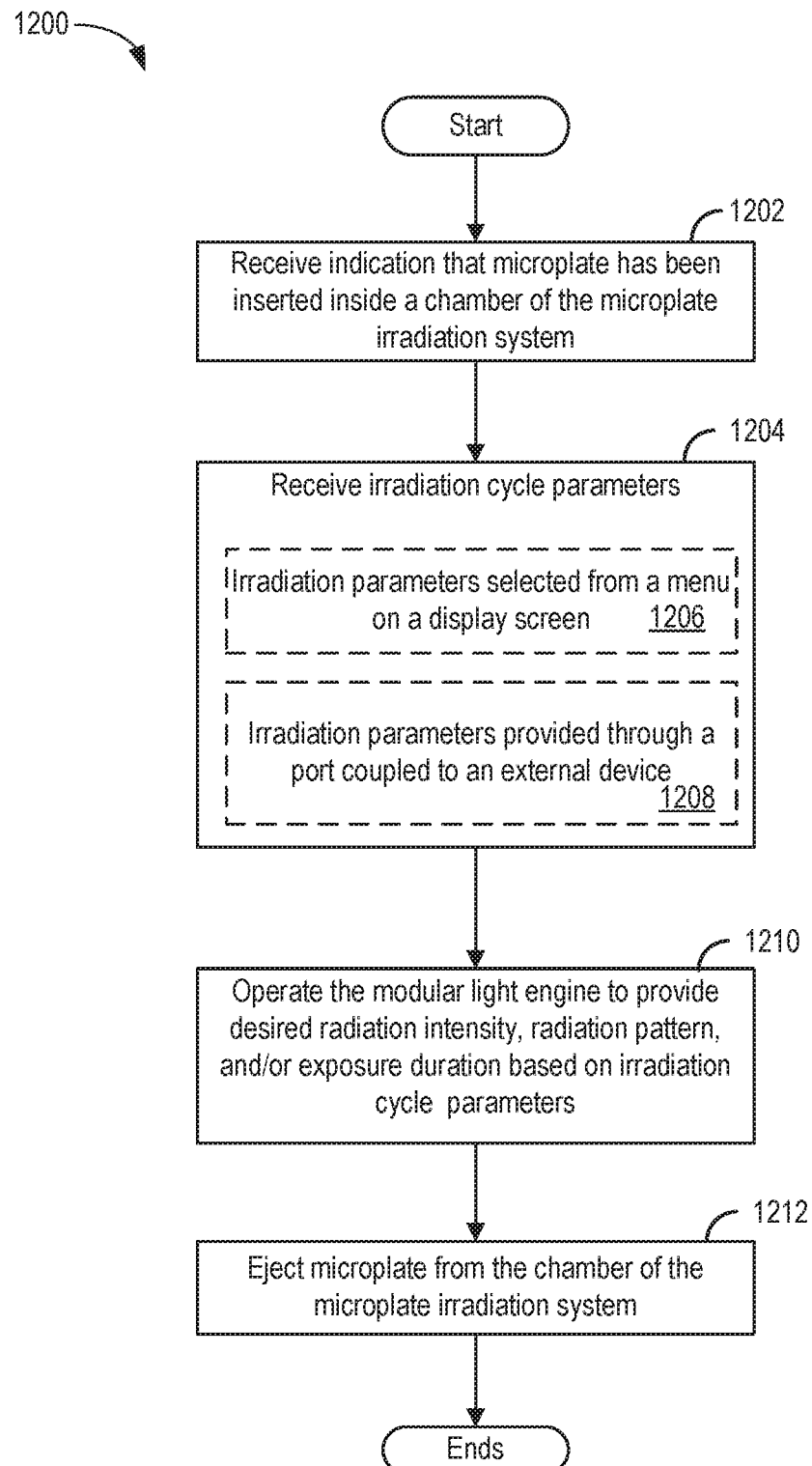
FIG. 12 illustrates an operating method for the bio-inactivation device with the microplate irradiation system.

A method 1200 for operating a microplate irradiation system is illustrated in a flowchart in FIG. 12. In one example the method 1200 may be used to operate the microplate irradiation system 10 and/or microplate irradiation system 100 illustrated in FIGS. 1-11. Instructions for carrying out the method 1200 may be executed by a controller, for example, the controller 14 of FIG. 1 and/or the controller 218 of FIGS. 2-3, based on instructions stored in the controller memory and in conjunction with signals received by the controller from the display screen 110, the port 120, the modular light engine 220 etc., illustrated in FIGS. 2-11.

The method 1200 begins by receiving an indication that a microplate has been inserted into a chamber of the microplate irradiation system. The microplate may be positioned inside a drawer extending out of the microplate irradiation system. The microplate wells may include liquid reagents. Hence, the microplate may be positioned on an even/flat surface of the drawer, such as a surface of stage 108, with the wells of the microplate facing away from the even surface. After the microplate is positioned inside the drawer, the drawer may be inserted back into a housing of the microplate irradiation system. In another example, reagent-holding devices such as microscopic slides, tissue culture plates, etc. may be inserted into the housing by placing the devices in the drawer. In another example, the microplate may be positioned directly inside the housing through an opening accessible through a door coupled to the opening. Once inside the housing, the microplate is positioned directly below the modular light engine, such that the modular light engine may direct light emission to the microplate without any physical and optical obstruction between the microplate and the modular light engine. Once the microplate is positioned inside the housing, ambient light and air flow through the opening is blocked, for example, by inserting the drawer all the way into the housing. The controller may receive an indication that the microplate has been inserted inside the drawer and the drawer has been closed based on a user input and/or based on detecting that the drawer has opened and then closed.

At 1204, the method 1200 includes receiving parameters for an irradiation cycle for irradiating the inserted microplate. In one example at 1206, the parameters may be received via a user input, for example the user may select the parameters using a display screen menu coupled to the microplate irradiation system and the selected parameters may be relayed to a controller, such as the controller 14 of FIG. 1. The selected parameters may include temporal duration, spatial pattern (by activation of specific light emitting devices), intensity level, dose (power), etc. In another example at 1208, the irradiation parameters may be received through a compatible external device, such as computer, a USB drive, etc., that may be relayed through a port of the microplate irradiation system to the controller.

At 1210, method 1200 includes operating the microplate irradiation system as per as the selected parameters to irradiate the microplate and the liquid reagents inside the microplate wells. The modular light engine may be activated to deliver germicidal UV radiation to the microplate at the selected intensity, dose, pattern, and duration. As explained previously, the modular light engine may include a plurality of light emitting devices, such as LEDs. Thus, one or more of the LEDs may be activated at a selected intensity, wavelength, and duration. Further, the selected pattern of light emission may be achieved by activating different subsets of the LEDs at different times and/or with different parameters. For example, all of the LEDs may be activated at the same time, with the same or varying intensities, wavelengths, and/or durations. In another example, a first subset of LEDs may be activated at a selected intensity, wavelength, and/or duration, while a second, different subset of LEDs may be activated at a different intensity, wavelength, and/or duration.

After the irradiation cycle is complete, the method 1200 proceeds to 1212 to eject the irradiated microplate from the housing of the microplate irradiation system. The microplate may be ejected automatically upon completion of the irradiation cycle or upon receiving a user input requesting the microplate be ejected. To eject the microplate, the drawer may be open and the user may then remove the microplate. Method 1200 then ends.

In this way, a controlled dose of germicidal UV may be delivered through a modular light engine including an array of light emitting diodes configured to direct germicidal UV to a microplate inside chamber of a microplate irradiation system.

In one example, the modular light engine may deliver a dose of germicidal light comprising multiple wavelengths (two or more) for inactivation. The multiple wavelengths used for inactivation may be selected based on contaminants to be inactivated, for example UVC light at 255 nm may target nucleic acids, UVC light at 275 nm may target protein stability by specifically targeting cysteine and aromatics, and UVA light at 365 nm may target lysine in proteins (e.g., enzymes such as RNase A). In some examples, certain contaminating microorganisms may demonstrate recovery (reactivation) after UV light exposure over time. In order to prevent this reactivation and to ensure an efficient and complete inactivation, two or more wavelengths of germicidal UV may be used. Additionally, wavelengths of light outside of the UV range may also be emitted (along with UV light, at least in some examples). For example, infrared (IR) light (e.g., at 1640 nm) may result in melting/disassociation of alpha helices while visible light (e.g., at 405 nm) may target common biological pigments (e.g., produced by microorganisms and therefore targeting such microorganisms).

Referring now to FIG. 13, a second embodiment of a bio-inactivation device is shown. The bio-inactivation device 1300 may be configured similarly to the bio-inactivation device of FIG. 1 but may be used as a compact hand-held illumination unit for surface disinfection without the microplate system. Such a device may be used as a point-of-use device for disinfecting surfaces and materials in one example. In another example, the bio-inactivation device of FIG. 13 may be incorporated in a larger light emission system for bio-inactivation applications (e.g., disinfection, DNA amplification, and sequencing). The device may be housed in housing 1301 and may include a control system 1326 (e.g., a processor and memory storing instructions executable by the processor), a modular light engine 1302 with one or more light emitting devices (e.g., LEDs) 1306, one or more user interfaces such as user interface 1330 (e.g., a mouse, keyboard, touch screen, display menu), and a communication system 1328 operable to couple the controller to one or more remote computing devices, for example.

The controller of the control system 1326 may be an electronic controller and may include a memory storing instructions executable to carry out one or more of the methods described herein. The controller may include one or more physical logic devices, such as one or more processors, configured to execute instructions. Additionally or alternatively, the controller may include hardware or firmware configured to carry out hardware or firmware instructions. The memory may include removable and/or built-in devices, including optical memory, solid-state memory, and/or magnetic memory. The memory may include; volatile, nonvolatile, static, dynamic, read/write, read-only, random-access, sequential-access, location-addressable, file-addressable, and/or content-addressable devices. The memory and logic device(s) may be integrated together into one or more hardware-logic components, such as field-programmable gate arrays (FPGAs). The control system 1326 may control the activation status (e.g., on or off) as well as the intensity of light emitted from each light emitter via coupling electronics 1322.

Bio-inactivation device 1300 may include a modular light engine 1302 comprising an array of light emitters 1306, such as light emitting diodes 1320 (LEDs), for example, or OLEDs, plasma discharge, or other light emitters. Each light emitter or group of emitters may be coupled directly or indirectly to power source 1324. Each light emitter or group of emitters may be coupled (e.g., mounted or bonded) to a substrate 1308. Substrate 1308 may further be coupled to a thermal device 1316, which may be an active thermal regulation system, such as a Peltier device, or may be a passive thermal regulation system, such as a heatsink. Modular light engine 1302 may be configured similarly to modular light engine 12 and/or 220, and as such includes a plurality of light emitting devices bonded to a substrate (e.g., comprising an array of LEDs), which is coupled to a heat sink with cooling fins. However, other configurations are possible.

A temperature sensor 1310 is shown coupled to substrate 1308 for measuring a temperature of the substrate. In other examples, the temperature sensor may be positioned to measure a temperature of one of the light sources directly and/or additional temperature sensors may be present. Output from temperature sensor 1310 may be used to control thermal device 1316 and/or the intensity of the light emitter(s) 1306. For example, if the output from the temperature sensor indicates that the light emitters are greater than a threshold temperature, the thermal device (if an active thermal device) may be activated to cool the light emitters and/or the intensity of light output by the light emitters may be decreased, to avoid degradation to the light emitters and/or other components. In yet other examples, temperature sensor 1310 may be omitted or coupled to a different component of the inactivation system.

The light emitted by one or more light emitters 1306 may travel along a light path to a treatment surface 1314. In some examples, the light traveling along the light path may pass through light transfer optics 1312 that may function to filter, focus, redirect, or otherwise condition the light to produce a desired illumination pattern, before reaching the treatment surface. The light transfer optics 1312 may include a bandpass filter, lenses (e.g., ball lens, collimating lens, Fresnel lens), collimators, light guides, and/or other optics.

As described earlier, the light produced by the light emitters 1306 may comprise multiple wavelengths (two or more) being incident on the treatment surface. The use of multiple wavelengths of light may extend the number of possible inactivation targets. For example, 255 nm UV light may target nucleic acids, 275 nm UV light may target protein stability by specifically targeting cysteine and aromatics, 365 nm UV light may target lysine in proteins (e.g., enzymes such as RNase A), while 405 nm visible light may target common biological pigments (e.g., produced by some microorganisms). As will be explained in more detail below, the use of multiple wavelengths at one time may be synergistic, as the effect of the combined wavelengths is greater than the sum of the effects of the individual wavelengths. As used herein, the term "multiple wavelengths of light" may refer to multiple peak or average wavelengths of light. For example, a light emitter configured to output light at 275 nm may actually output light at 275 nm plus light in a wavelength range around 275 nm, such as light from 270-280 nm. Likewise, a light emitter configured to output light at 365 nm may actually output light at 365 nm plus light in a wavelength range around 365 nm, such as 360-370 nm. As such, when reference is made to multiple wavelengths of light herein, the multiple wavelengths may be different peak or average wavelengths output from different light emitters, for example.

In one example, a specified excitation wavelength of light ($\lambda$ EX, 1332 of single or multiple wavelengths) may be emitted from the modular light engine of the bio-inactivation device that may be incident on treatment surface 1314. When illuminated with an excitation source of a specified wavelength 1332, organisms, proteins, and/or other contaminants present on the surface may exhibit fluorescence. Fluorescence refers to molecular absorption of light at a first wavelength and its nearly instantaneous re-emission at a second, longer wavelength. For example, light of the excitation wavelength emitted by light emitters 1306 may be absorbed by organisms on the illuminated surface causing electrons in the organism to move to a higher energy, excited state. As the electrons recede back down to their lower energy, ground state, energy is released as a photon of light at the second, longer wavelength. The amount and the wavelength of the fluorescence emitted by the organisms may depend upon the molecular makeup of the cell (e.g., type of microorganism) and the wavelengths of light used for excitation/illumination. Upon exposure to germicidal wavelengths of UV, IR, and/or visible radiation, the molecular makeup of a cell including its nucleic acids are irreversibly altered causing the level of fluorescence to decrease. In one example, when the treatment surface and hence any contaminating microorganisms and/or molecules are exposed to multiple germicidal wavelengths of radiation targeting different aspects of an organism (e.g., proteins, nucleic acids, etc.), the level of fluorescence may be seen to decrease.

Thus, in order to measure the fluorescence (e.g., intensity level and wavelength of the emitted light), one or more signal detectors may be included in the bio-inactivation device that may be configured to detect light emission at the second, longer wavelength emission $\lambda$ EM_(1334) as fluorescence. In one example, the fluorescence signal detector may be a photodetector 1318 (e.g., semiconductor photodiode). The bio-inactivation device may be coupled to photodetector 1318 which may be housed within the bio-inactivation device and further be communicatively coupled to the control system. During bio-inactivation device operation, photodetector 1318 may convert a detected amount/intensity and wavelength of emitted light into electrical current and transmit it to control system 1326 as a measure of fluorescence from surface 1314. In some examples, the incident and/or emitted light may include a spectrum of wavelengths (two or more wavelengths) and it may be desirable to detect a range of wavelengths. Additionally, the fluorescence signal detector may comprise a photodetector with an integral filter to reduce unwanted spectral emission (e.g., noise from wavelengths outside the desirable range of wavelengths being measured), and enhance the signal-to-noise ratio (SNR).

By measuring the change in fluorescence using the photodetector (before and after multi-wavelength light exposure), the bio-inactivation device of FIG. 13 may enable the user to determine the presence and amounts of microorganisms on surface 1314. Fluorescence from the surface may be measured by the photodetector prior to germicidal light exposure, and fluorescence information may be transmitted to and stored in the memory of the control system. The surface may then be exposed to germicidal light of a desired intensity, desired dose, and desired pattern of irradiation for a specified duration of time. In one example, irradiation parameters may be selected by a user using a menu on a display screen coupled to the bio-inactivation device, e.g., user interface 1330, or may be received via an external device, e.g., external device 1328. Following light exposure, fluorescence from the treated surface may be detected and measured by the photodetector and the information relayed to the control system. The control system may then compare the fluorescence measurements taken prior to and after light treatment of the treatment surface and assess if inactivation of contaminants on the surface was achieved.

In some examples, the output from the photodetector may be monitored continuously (or nearly continuously) during the emission of the germicidal light to track the inactivation of the microorganisms and/or molecular contaminants on the treatment surface. The germicidal light emission may be deactivated once the detected fluorescence meets a threshold condition for the surface contaminants (e.g., drops below an inactivation threshold).

While the multiple wavelengths of light output from the modular light engine and fluorescence feedback control were described above with respect to a hand-held device, other configurations are possible. For example, the bio-inactivation device in the form of a microplate irradiation system 10 including a modular light engine 12 of FIG. 1 may be configured similarly to the modular light engine 1302 of the bio-inactivation device 1300 of FIG. 13, such that multiple wavelengths of light may be output from modular light engine 12 to a microplate. Further, microplate irradiation system 10 may include a photodetector, similar to photodetector 1318, in order to measure fluorescence emitted by microorganisms on a surface of the microplate and adjust the light intensity, duration of exposure, etc., based on the fluorescence as described in more detail below. In alternative embodiments, the bio-inactivation device may be part of a lighting system of a tissue culture hood or other work space, a portable hollow unit, e.g., a box fitted with UV-emitting LEDs, such that materials to be sterilized (e.g., remote controls, keys, cordless phones, cell phones, etc.) may be dropped inside the box for a defined period of time or other device.

FIG. 15 illustrates a method 1500 for determining bio-inactivation using multi-wavelength germicidal light based on fluorescence using a bio-inactivation device, such as the bio-inactivation device of FIG. 13. In one example, method 1500 may be used to operate the bio-inactivation device of FIG. 1 including the microplate irradiation system. Instructions for carrying out method 1500 may be executed by a controller, for example, the control system 1326 of FIG. 13 or the controller 14 of FIG. 1, based on instructions stored in the memory of the controller and in conjunction with signals received at the controller.

At 1502, method 1500 begins by illuminating a surface with an excitation light source of a specified wavelength $\lambda$ EX (single or multiple wavelengths of excitation). The surface being illuminated may be any surface on which the bio-inactivation device may be positioned. The excitation source may comprise of one or more desired wavelengths of illumination such that when emitted back from the surface at a higher wavelength, a level of fluorescence emanating from the surface to be treated may be obtained.

At 1504, method 1500 may measure an initial fluorescence level based on an amount and wavelength of light emitted from surface illuminated with excitation source ($\lambda$ EM) using a photodetector, e.g., photodetector 1318 of FIG. 13. The initial fluorescence may be detected and measured by the photodetector of the bio-inactivation device prior to treatment of the surface with multi-wavelength germicidal radiation. The measured initial fluorescence information may be relayed and stored in the memory of the controller.

At 1506, method 1500 may receive irradiation cycle parameters. The irradiation cycle parameters may include a desired intensity of irradiation, a desired dose, a desired pattern of irradiation, and/or a duration of exposure for which the surface to be treated is to be exposed to germicidal irradiation. In one example, the irradiation cycle parameters may be received via user input, as indicated at 1508, for example the user may select the irradiation parameters from a menu on a display screen. In another example, the irradiation cycle parameters may be received through a port coupled to an external device, as indicated at 1510. For example, the parameters may be pre-set by a user and may be stored on an external device e.g., a USB drive.

Additionally, as indicated at 1511, the method may include determining constituent wavelengths to be used for bio-inactivation based on target surface contaminants. The multiple constituent wavelengths selected may depend upon the target(s) to be bio inactivated. The target(s) may be an enzyme in one example (e.g., RNase A) and the optimal wavelengths selected for inactivation may be further based on the relative absorption characteristics of the target (e.g., RNase A enzyme) and its chemical bonds being targeted. Furthermore, microorganisms may differ in their cellular makeup, for example some microorganisms may show susceptibility to specific wavelengths of light on account of possessing a certain subset of compounds that may be targeted by the specific wavelength of light, while being resistant to others. For example, 255 nm UV light may target nucleic acids, 275 nm UV light may target protein stability via targeting cysteine and aromatics, 365 nm UV light may target lysine in proteins, while 405 nm visible light may target common biological pigments. In one example, a combination of UV light at 275 nm and 365 nm may be selected for inactivation while in another example a combination of UV at 255 nm and 275 nm may be chosen. The optimal constituent wavelengths selected may therefore be based on prior knowledge of the type of organisms present on the contaminated surface, and therefore their cellular makeup for example. The target surface contaminants may be determined based on the received irradiation cycle parameters, e.g., a user may enter an input specifying the target surface contaminants.

Once the irradiation cycle parameters have been selected, method 1500 may proceed to 1512 to operate the bio-inactivation system with desired radiation intensity, radiation pattern, and/or exposure duration based on irradiation cycle parameters set at 1506 above. The bio-inactivation device may irradiate a surface to be treated with germicidal light with the selected irradiation cycle parameters described above. Operating the bio-inactivation system may include activating one or more light emitters, such as the LEDs described above, at the specified intensity, pattern, duration, and wavelength(s). In examples where multiple wavelengths of light are to be emitted, a first subset of LEDs may be controlled to output light of a first wavelength (e.g., 275 nm) while a second subset of LEDs may be controlled to output light of a second wavelength (e.g., 365 nm). To ensure even coverage of both wavelengths of output light across the entire treatment surface, the different subsets of LEDs may be interweaved, for example the first subset of LEDs may alternate rows with the second subset of LEDs, alternate columns with the second subset of LEDs, etc.

Method 1500 may detect inactivation by measuring the fluorescence level after exposure, based on an amount and wavelength of emitted light from surface λ EM using a photodetector at 1514. As mentioned earlier with reference to FIG. 13, an amount and wavelength of emitted light (measured as fluorescence) may be based on the molecular makeup of biological organisms and other contaminants present on the surface. Upon exposure to light in the germicidal wavelength range, molecular contaminants present on the surface or within cells of organisms present on the surface may be irreversibly altered/disrupted, leading to loss or decrease of fluorescence. Thus, the photodetector may measure a level of fluorescence of the surface after treatment and fluorescence information may be relayed to the controller in real time, allowing a real time estimation of the reduction in fluorescence indicative of inactivation of molecular contaminants or microorganisms.

At 1516, method 1500 may determine if the change in fluorescence level (initial vs. after exposure) is greater than a pre-determined threshold. The threshold at 1516 may be a non-zero threshold and may represent a change in fluorescence value above which inactivation of contaminants and/or microorganisms may be successfully achieved. The change in fluorescence may be calculated by the controller. The controller may calculate a difference (e.g., change) based on initial fluorescence (obtained at 1504 above and stored in the memory of the controller) and fluorescence after germicidal light exposure (from 1514).

If the change in fluorescence is not determined to be greater than the threshold (e.g., NO at 1516), method 1500 may adjust the bio-inactivation system operating parameters (e.g., adjust radiation intensity, radiation pattern and/or exposure duration) at 1518. In one example, a change in fluorescence not greater than the threshold may indicate that inactivation with the selected radiation parameters including the multiple wavelengths was unsuccessful (e.g., microorganisms and/or other contaminants were not successfully inactivated). In another example, a change in fluorescence below the threshold may indicate partial inactivation with the selected radiation parameters (e.g., microorganisms and/or other contaminants were not completely inactivated or all microorganisms and contaminants were not inactivated). In one example, the bio-inactivation system operating parameters of radiation intensity, pattern, and/or duration of exposure may be adjusted (e.g., the duration may be increased in one example). In another example, alternative multiple wavelengths or additional wavelengths targeting other aspects of the microorganisms may be selected and method 1500 be carried out again.

For example, a first fluorescence response may indicate inactivation of one type of microorganism (e.g., bacteria) while a second fluorescence response may indicate incomplete inactivation of a different type of microorganism (e.g., virus). Accordingly, if the first fluorescence response is observed (e.g., a first change in fluorescence level at a given excitation wavelength), it may be determined that bacteria on the treatment surface have been inactivated. If a second fluorescence response is also observed (e.g., a second change in fluorescence at a different excitation wavelength), it may be determined that virus on the inactivation surface has been only partially inactivated. At that point, the system may change the wavelength(s) and/or intensity of light output for viral inactivation. Method 1500 may then loop back to 1512 to operate the bio-inactivation system with the desired wavelengths, radiation intensity, radiation pattern, and/or exposure duration based on irradiation cycle parameters. In still further examples, the system may automatically determine target contaminants present on the treatment surface based on the detected fluorescence prior to output of the germicidal light. For the example, the system may determine that both bacteria and virus are present on the surface based on the initial detected fluorescence. The system may then automatically select one or more wavelengths of germicidal light to be output and may adjust the wavelength(s) and/or intensity of the germicidal light during the course of the sterilization process to target all the identified contaminants on the surface. In still further examples, a first contaminant may be initially detected and once the first contaminant has been fully inactivated, the remaining fluorescence signal may indicate the presence of a second, different contaminant still on the treatment surface.

Thus, the bio-inactivation device described herein may improve inactivation of different kinds of microorganisms by changing parameters within an irradiation cycle or dynamically adapting the irradiation parameters. As an example, a target surface may have a relatively large number of bacteria and a relatively small number of virus. The surface itself may be mildly susceptible to damage when exposed to light in the UV-A range, so a purely UV-C inactivation recipe may be selected (e.g., the surface may be comprised of a plastic paraffin film or other material prone to degrading when exposed to light in the UV-A range). The fluorescence emitted by the large number of active bacteria may obscure the presence of the virus, until most of the bacteria are inactivated by the UV-C irradiation cycle and the viral load is able to be detected. At that point, the bio-inactivation device may prompt the user to select a more effective virus-inactivating recipe, or the bio-inactivation device may be configured to automatically enable a short, dual-wavelength UV-A/UV-C cycle that is more effective against virus. Accordingly, the treatment surface material composition may also be taken into account when selecting appropriate irradiation cycle parameters.

On the other hand, if the change in fluorescence is determined to be greater than the threshold (e.g., YES at 1516), method 1500 may move to 1520 to display inactivation data to user. In one example, inactivation data may include a level of inactivation as determined by the change in fluorescence (e.g., percentage change). Method 1500 may continue to 1522 to deactivate the modular light engine of the bio-inactivation device, by deactivating the LEDs for example. Method 1500 then returns.

In this way, bio-inactivation of microorganisms based on real time fluorescence feedback using the bio-inactivation device may be determined and operating radiation parameters may be accordingly adjusted to achieve complete and rapid inactivation.

Referring now to FIG. 14, a third embodiment of a bio-inactivation device is shown. The bio-inactivation device 1400 may be configured similar to the bio-inactivation device of FIG. 1 but may be used as a compact hand-held illumination unit for surface disinfection without the microplate system, similar to the embodiment shown in FIG. 13. Such a device may be used at a point-of-use for disinfecting surfaces and materials and may be optionally incorporated in larger light emission system for bio-inactivation applications. Device 1400 may be housed in housing 1401 and may include a control system 1426 (e.g., including a processor and memory), a modular light engine 1402 with one or more light emitting devices (e.g., LEDs) 1406, one or more user interfaces such as user interface 1430 (e.g., a mouse, keyboard, touch screen, display menu), and a communication system 1428 operable to couple the controller to one or more remote computing devices, for example. The controller of the control system 1426 may be an electronic controller and may include a memory, storing instructions executable to carry out one or more of the methods described herein. The control system 1426 may control the activation status (e.g., on or off) as well as the intensity of light emitted from each light emitter via coupling electronics 1422.

Bio-inactivation device 1400 may include a modular light engine 1402 comprising an array of light emitters 1406 that may be light emitting diodes 1420 (LEDs), for example. Each light emitter may be coupled directly or indirectly to power source 1424 and may be coupled to a substrate 1408. Substrate 1408 may further be coupled to a thermal device 1416, which may be an active or a passive thermal regulation system. A temperature sensor 1410 is shown coupled to substrate 1408 for measuring a temperature of the substrate. In other examples, the temperature sensor may be positioned to measure a temperature of one of the light sources directly and/or additional temperature sensors may be present. Output from temperature sensor 1410 may be used to control thermal device 1416 and/or the intensity of the light emitter(s) 1406. In yet other examples, temperature sensor 1410 may be omitted or coupled to a different component of the inactivation system.

The light emitted by one or more light emitters 1406 may travel along a light path to a treatment surface 1414. In some examples, the light traveling along the light path may pass through light transfer optics 1412 including a filter, lenses and/or other optics that may function to filter, focus, redirect, or otherwise condition the light to produce a desired illumination pattern. As described earlier, the light produced by the light emitters 1406 may comprise multiple wavelengths (two or more) being incident on the treatment surface. The emission of multiple wavelengths of light may extend the number of possible inactivation targets, for example 255 nm UV light may target nucleic acids, 275 nm UV light may target protein stability by specifically targeting cysteine and aromatics, 365 nm UV light may target lysine in proteins while 405 nm light may target common biological pigments (e.g., produced by some microorganisms). Further, the use of multiple light wavelengths at one time may be synergistic, as the effect of the combined wavelengths is greater than the sum of the effects of the individual wavelengths.

In one example, a specified wavelength of light $\lambda_0$ may be emitted from the modular light engine of the bio-inactivation device that may be incident ($I_0$) on treatment surface 1414. When illuminated with an excitation source of a specified wavelength $\lambda_0$, living (e.g., intact) microorganisms present on the surface may reflect the light differently when compared to a dead (e.g., inactive) microorganisms. Typically, dead microorganisms lose their cellular integrity (e.g., cell membrane, cell wall, or coat integrity may be disrupted), allowing their contents to spread out on the surface, and may therefore reflect light differently than their living counterparts. This spreading of cellular contents may be detectable as a change in optical properties (e.g., a decrease or an increase in reflectance) of the surface. In one example, when the surface contaminants are exposed to multiple germicidal wavelengths of radiation targeting different aspects of an organism (e.g., proteins, nucleic acids, etc.), the reflectance may be seen to change.

In one example, the bio-inactivation device of FIG. 14 may use this criterion to assess a level of inactivation for a given surface. For example, a surface may be illuminated with light of a specific wavelength and an initial reflectance I based on an amount of reflected light may be measured. Germicidal irradiation parameters may then be selected. In one example, the germicidal irradiation parameters may be selected based on the amount of reflected light, e.g., the reflected light may indicate relative levels and/or types of contaminants on the treatment surface. The surface may then be exposed to multiple wavelengths of germicidal light of a desired intensity, desired dose, and desired pattern of irradiation for a specified time duration. In one example, irradiation parameters including a combination of wavelengths to be used for bio-inactivation may be selected using a menu on a display screen coupled to the bio-inactivation device, e.g., user interface 1430, or may be selected via an external device, e.g., external device 1428. The bio-inactivation device may be operated with the selected parameters to inactivate microorganisms on the given surface by UV and/or other light exposure. After exposure, the surface may once again be illuminated with light (e.g., of a specific wavelength, used before to measure initial reflectance) and a reflectance after exposure to germicidal light may be measured. Based on a change in reflectance from before multi-wavelength light exposure to after bio-inactivation with multi-wavelength light, a level of inactivation of microorganisms on the surface may be evaluated.

In order to measure an amount of reflected light, one or more signal detectors with an optional filter may be included in the bio-inactivation device 1400 configured to detect reflectance before and after germicidal light exposure from surface 1414. In one example, the reflectance detector may be a photodetector (e.g., semiconductor photodiode with an optional integrated filter), such as photodetector 1418. In one example, an additional photodetector configured to measure fluorescence may also be present. The photodetector may be housed within the bio-inactivation device and be communicatively coupled to the control system. During bio-inactivation device operation, photodetector 1418 may convert a detected amount of reflected light into electrical current and transmit it to control system 13426 as a measure of reflectance from surface 1414.

In this way, following light exposure, reflectance from the treated surface may be detected and measured by the photodetector and the information relayed to the control system. The control system may then compare the reflectance measurements taken prior to and after light treatment of the treatment surface and assess if inactivation of contaminants on the surface was achieved.

In some examples, the output from the photodetector may be monitored continuously (or nearly continuously) during the emission of the germicidal light to track the inactivation of the microorganisms and/or molecular contaminants on the treatment surface. Once the detected reflectance meets a condition relative to a threshold (e.g., changes beyond a threshold indicating inactivation of the contaminants on the treatment surface), the germicidal light emission may be deactivated.

While the multiple wavelengths of light output from the modular light engine and reflectance feedback are described above with respect to a hand-held device, other configurations are possible. For example, the bio-inactivation device in the form of a microplate irradiation system 10 including a modular light engine 12 of FIG. 1 may be configured similarly to the modular light engine 1402 of the bio-inactivation device 1400 of FIG. 14, such that multiple wavelengths of light may be output from modular light engine 12 to a microplate. Further, microplate irradiation system 10 may include a photodetector, similar to photodetector 1418, in order to measure fluorescence emitted by microorganisms or other molecular contaminants on a surface of the microplate and adjust the light intensity, duration of exposure, etc., based on the reflectance as described in more detail below.

FIG. 16 illustrates a method 1600 for determining bio-inactivation based on reflectance in accordance with the bio-inactivation device of FIG. 14. In one example, method 1600 may be used to operate the bio-inactivation device of FIG. 1 including the microplate irradiation system. In another example, method 1600 may also operate the bio-inactivation device of FIG. 13. Instructions for carrying out method 1600 may be executed by a controller, for example, the control system 1426 of FIG. 14, control system 1326 of FIG. 13 or the controller 14 of FIG. 1, based on instructions stored in the memory of the controller and in conjunction with signals received at the controller.

At 1602, method 1600 begins by illuminating a surface with an excitation light source of a specified wavelength. The specified wavelength may be one that is selected based on a robust signal to noise ratio. Upon illumination of the surface (e.g., surface contaminated with microorganisms and/or other contaminants), light striking the surface may be reflected back to the bio-inactivation device in an amount/direction based on the presence, amount, and cellular integrity of the constituents of the surface. The light that is emitted for the reflectance measurement may be the same wavelength or a different wavelength than the light emitted for sterilizing the treatment surface, as explained below.

At 1604, method 1600 may measure an initial reflectance $I_o$ based on an amount of reflected light from the surface using a photodetector. In one example, the amount of reflected light may be proportional to an amount of intact microorganisms present on the surface. The reflected light (e.g., reflectance) measured may include a constant reflectance from the surface. The initial reflectance may be measured by the photodetector of the bio-inactivation device prior to the surface being exposed to germicidal radiation. This could be considered as background light, which may then be stored in controller memory.

At 1606, method 1600 may select irradiation cycle parameters. The irradiation cycle parameters may include a desired intensity of irradiation, a desired dose, a desired pattern of irradiation, and/or a duration of exposure for which the surface to be treated is to be exposed to germicidal irradiation. In one example, the irradiation cycle parameters may be received via user input, as indicated at 1608, for example the user may select the irradiation parameters from a menu on a display screen. In another example, the irradiation cycle parameters may be received through a port coupled to an external device, as indicated at 1610. For example, the parameters may be pre-set by a user and may be stored on an external device, e.g., a USB drive.

Receiving the irradiation cycle parameters may also include determining constituent wavelengths (multiple) to be used for bio-inactivation based on target surface contaminants, as indicated at 1611. The multiple constituent wavelengths selected may depend upon the target to be bio inactivated, e.g., an enzyme such as RNase A. The optimal wavelengths selected for inactivation may be further based on the relative absorption characteristics of the target (e.g., enzyme) and the chemical bonds being targeted. Furthermore, microorganisms may vary in their cellular makeup. Some microorganisms may show susceptibility to specific wavelengths as a consequence of possessing a certain subset of compounds that may be targeted by the specific wavelength of light, while being resistant to others. For example, 255 nm UVC light may target nucleic acids, 275 nm UVC light may target protein stability via targeting cysteine and aromatics, 365 nm UVA light may target lysine in proteins, while 405 nm visible light may target common biological pigments.

Once the irradiation cycle parameters have been selected, method 1600 may proceed to 1612 to operate the bio-inactivation system with desired radiation intensity, radiation pattern, and/or exposure duration based on irradiation cycle parameters set at 1606 above. The bio-inactivation device may irradiate a surface to be treated with multiple wavelengths of germicidal light with the selected irradiation cycle parameters. Operating the bio-inactivation system may include activating one or more light emitters, such as the LEDs described above, at the specified LED intensity, spatial pattern, time duration, and wavelength(s). In examples where multiple wavelengths of light are to be emitted, a first subset of LEDs may be controlled to output light of a first wavelength (e.g., 275 nm) while a second subset of LEDs may be controlled to output light of a second wavelength (e.g., 365 nm). Uniform spatial coverage of all wavelengths may be ensured by alternating respective LEDs or groups of LEDs in their positional layout (e.g., 275 nm column/row followed by 365 nm column/row, etc.), comprising the overall group (i.e. array).

At 1614, method 1600 may illuminate the surface with the excitation light source of a specified wavelength. As mentioned earlier in FIG. 14, an amount of reflected light (measured as reflectance) may be based on an amount of and the cellular integrity of microorganisms present on the surface. Upon exposure to multiple wavelengths of light in the germicidal range, microorganisms present on the surface may be inactivated, leading to loss of cellular integrity and therefore loss of reflectance (e.g., decrease in reflectance). The subsequent variance in light reflected from the cellular surface to the photodetector, and resulting change in photodetector signal (voltage) may be relayed to the controller, allowing a real time measure of the relative change in reflectance.

At 1616, method 1600 may measure reflectance after bio-inactivation based on an amount of reflected light from the surface using a photodetector. The reflectance may be proportional to an amount of microorganisms present on the surface, which after bio-inactivation (e.g., due to UV exposure), may be expected to decrease. The measured reflectance may also include a contribution from the surface, which may be a constant value. The measured reflectance data after bio-inactivation may be relayed to and stored in the memory of the controller. Method 1600 may calculate a change in reflectance ($I_0$–I) I) at 1618. The controller of the bio-inactivation device may perform this calculation based on the initial reflectance $I_0$ obtained at 1604 and reflectance I obtained at 1616 after exposing the surface with germicidal light.

At 1620, method 1600 may determine if the change in reflectance ($I_0$–I) is greater than a threshold. The threshold at 1620 may be a pre-determined non-zero threshold and may represent a change in reflectance above which inactivation of microorganisms on the surface may be successfully achieved. If the change in reflectance is not determined to be greater than the threshold (e.g., NO at 1620), method 1600 may adjust the bio-inactivation system operating parameters (e.g., adjust radiation intensity, radiation pattern and/or exposure duration) at 1622. In one example, a change in reflectance not greater than the threshold may indicate that inactivation with the selected radiation parameters was unsuccessful (e.g., microorganisms were not successfully inactivated). In another example, a change in reflectance not greater than the threshold may indicate partial inactivation with the selected radiation parameters (e.g., microorganisms were not completely inactivated or all microorganisms were not inactivated). In one example, the bio-inactivation system operating parameters of radiation intensity, spatial pattern, and/or duration of exposure may be adjusted (e.g., increased in one example). In another example, alternative multiple wavelengths or additional wavelengths targeting other aspects of the microorganisms may be selected and method 1600 be carried out again.

For example, as explained above with respect to FIG. 15, a given reflectance (e.g., a given change in reflectance at a given wavelength or intensity of light) may indicate full inactivation of one microorganism but not another (e.g., full inactivation of bacteria but partial inactivation of virus). In such examples, the wavelength(s) and/or intensity of germicidal light may be adjusted. In another example, the user may specify a low-intensity longer cycle for a more "gentle" treatment of sensitive materials. For such a cycle, a long duration of low-intensity blue light (405 nm) may be effective against bacteria. However, if the sensors detect the presence of active virus (e.g., based on the reflectance signal), the user may elect to include a short duration of high-intensity 275 nm light or 275 nm and 365 nm light that is more effective against virus. Method 1600 may then loop back to 1612 to operate the bio-inactivation system with the desired wavelengths, radiation intensity, spatial pattern, and/or exposure duration based on irradiation cycle parameters.

On the other hand, if the change in reflectance is determined to be greater than the threshold (e.g., YES at 1620), method 1600 may move to 1624 to display inactivation data to user. In one example, inactivation data may include a level of inactivation as determined by the change in reflectance (e.g., percentage change). Method 1600 may continue to 1626 to deactivate the modular light engine of the bio-inactivation device, by deactivating the LEDs for example. Method 1600 then returns.

In this way, bio-inactivation of microorganisms based on real time reflectance feedback using the bio-inactivation device may be determined and operating radiation parameters may be accordingly adjusted to achieve complete and rapid inactivation.

In one example, each light emitter of the bio-inactivation device of FIG. 1, 13, or 14 may emit light of a single wavelength or variable wavelengths, as dictated by the controller. Most inactivation methods and systems currently in use utilize a single UV wavelength to achieve inactivation of specific targets (e.g., inactivation of nucleic acids may be optimally performed at 255 nm, inactivation of enzymes may be performed at 275 nm to target cysteine and aromatics, etc.). In some situations, inactivated targets (e.g., enzymes, microorganisms), especially those inactivated by a single germicidal UV wavelength may demonstrate recovery (reactivation) after UV exposure, over a period of time.

An example of a ubiquitous molecular contaminant frequently found on surfaces in the laboratory includes the ribonuclease enzyme protein RNase A. RNase A is not only a very stable enzyme, highly resistant to denaturation (disruption of protein) but is also found as a frequent contaminant during automated DNA sequencing and amplification. RNase A, even when found in trace amounts in reagents and buffers used for sequencing and amplification of DNA, may interfere with experimentation and compromise results; RNase A targets RNA so it also desirable to remove even trace amounts of RNase A when performing work with RNA. Diethylpyrocarbonate (DEPC) treatment is the most common method used to inactivate RNases in water and other reagents. However, DEPC treatment is not only time consuming (e.g., may require sample with DEPC to sit overnight) but can also produce secondary chemicals not suitable for automated DNA analysis. Thus, RNase A serves as a suitable target to ascertain the validity of the bio-inactivation device using multiple wavelengths of germicidal light to achieve a complete and effective inactivation. In one example, a combination of UV light at 275 nm and 365 nm wavelengths may be used to target RNase A. As previously described, 275 nm UVC light may target protein stability by specifically targeting cysteine and aromatics while 365 nm UVA light may target lysine in proteins. FIG. 17 shows RNase A enzyme activity measured as relative fluorescence, when a surface contaminated with RNase A is treated with various intensities (irradiance) of UV light at 275 nm wavelength, for a specific time duration. The horizontal axis (x-axis) denotes time after exposure (to the UV light) and the vertical axis (y-axis) denotes RNase A enzyme activity as relative fluorescence. Line 1702 shows a positive control, e.g., an intact and active RNase A, not subjected to UV light exposure. Line 1714 shows a negative control, e.g., a sample containing no RNase A. Lines 1704, 1706, 1708, 1710, and 1712 all show RNase A activity after a five minute exposure to increasing intensities of UV irradiance as marked on the figure legend.

In order to test the ability of the bio-inactivation device to permanently inactivate RNase A, a contaminated surface with RNase A was exposed to 275 nm UVC light emitted from the modular light engine of the bio-inactivation device. The duration of exposure was fixed at five minutes, with subsequent measurement of RNase A enzyme reactivation activity (relative fluorescence), over a period of time as shown by the x axis in FIG. 17. Line 1704 shows significant RNase A activity (e.g., the enzyme is functional with almost complete reactivation), after being exposed for five minutes to 275 nm UVC light at 10% irradiance (63.5 mW/cm$^2$). When the irradiance of 275 nm UVC light was increased to 25%, a decrease in RNase A reactivation was observed (compared to 10% irradiance), as shown by line 1706. As the irradiance of 275 nm UVC light was increased to 50% and subsequently to 75%, RNase A reactivation significantly decreased indicating nearly complete enzyme inactivation (e.g., denaturation or chemical modification of the enzyme), with 50% irradiance (316.7 mW/cm$^2$) successfully inhibiting enzyme activity, shown by lines 1708 and 1710, respectively. 275 nm UVC light at 100% irradiance (635.4 mW/cm$^2$) was effective in achieving complete inactivation of RNase A, with no detectable enzyme reactivation when assayed over a period of time as shown by line 1712, similar to the negative control (line 1714).

As seen from line 1708, 50% irradiance of 275 nm UV light for a time period of five minutes led to a significant decrease in RNase A enzyme activity with nearly complete inactivation (e.g., denaturation of the enzyme). In one example, the dose of UV light may impact the inactivation at a given wavelength and irradiance, and may be controlled by either changing the irradiance (as seen in FIG. 17) or by changing duration of exposure (as shown in FIG. 18).

FIG. 18 shows RNase A enzyme activity when the surface with RNase A is treated over increasing durations of exposure with 275 nm UVC light at 50% irradiance. The horizontal axis (x-axis) denotes exposure time (to UV light) and the vertical axis (y-axis) denotes RNase A enzyme activity in relative fluorescence units. Line 1802 shows a steady decrease in enzyme activity when a surface contaminated with RNase A is subjected to increasing exposure durations (doses) of 275 nm UVC light at 50% irradiance. Changing (e.g., increasing) the exposure time to effectively provide a single dose of UVC light at 275 nm at 50% irradiance may yield the same results as exposing the surface to UVC light at 275 nm with an irradiance level above 50% (e.g., 75%, 100%).

As previously described, some microorganisms may exhibit resistance to a single (selected) wavelength of UV light. In some situations, certain microorganisms may even demonstrate recovery (reactivation) after sufficiently long UV exposure over time, rendering the single UV wavelength exposure ineffective. Reactivation may depend upon the type of microorganism and various environmental conditions such as light, temperature, etc. Such reactivation of microorganisms may also rely on enzymes and has been observed for various microorganisms such as bacteria, virus, several protein vectors, fungi, etc. Different microorganisms comprised of different enzymes, different cell membrane structures, etc., may be susceptible to different wavelengths of light (e.g., a given microorganism may be susceptible at one wavelength of light but resistant at another). Similarly, some macromolecules may exhibit inactivation susceptibility at some wavelengths while showing resistance at others.

In order to ensure complete and efficient inactivation, two or more wavelengths of light targeting different structures or pathways within organisms may be utilized, leading to a synergistic effect as depicted by FIG. 19. Referring now to FIG. 19, a graph 1900 depicting the synergistic effect of using multiple UV wavelengths on RNase A enzyme activity is shown. The horizontal (X) axis denotes UV exposure time and the vertical (Y) axis denotes relative RNase A enzyme activity based on fluorescence efficacy. Line 1908 shows a positive control (e.g., an intact and functional RNase A) unexposed to any UV light and therefore showing no affected enzyme activity. Line 1910 shows the relative fluorescence of RNase A after exposure to 365 nm UVA light (measured irradiance level of 10.1 mW/cm$^2$). Line 1902 shows the inactivation of RNase A as a function of time when exposed to UVC light at 275 nm at ~50% intensity (a measured irradiance level of 316.7 mW/cm$^2$). Line 1904 shows the inactivation of RNase A as a function of time when exposed to UVC light at 275 nm at 100% intensity (measured irradiance level of 635.4 mW/cm$^2$). Line 1906 shows the inactivation of RNase A as a function of time when exposed to a combination of wavelengths using 275 nm UVC at 50% irradiance (316.7 mW/cm$^2$) and 365 nm UVA (10.1 W/cm$^2$).

As seen from graph 1900, RNase A activity gradually declined and the enzyme was completely inactivated after 15 minutes exposure with 275 nm UVC light at approximately a 50% irradiance level as seen from the relative fluorescence values depicted by line 1902. In contrast, RNase A was completely inactivated after a one minute exposure with 275 nm UVC light at 100% irradiance. However, as shown and explained in FIG. 17, several microorganisms may demonstrate recovery (reactivation) over time following UV exposure. In order to prevent such reactivation and to enable a more efficient and complete inactivation, two or more wavelengths of UV light may be utilized to target different aspects of an organism or an enzyme (e.g., RNase A). As seen from line 1906 of graph 1900, concurrent exposure of RNase A with two UV wavelengths (i.e. 275 nm and 365 nm) resulted in a more rapid inactivation. RNase A enzyme was completely inactivated after three minutes, as measured by fluorescence. The combination of wavelengths was successful in achieving complete inactivation at a lower irradiance (50%) of UVC light at 275 nm. Furthermore, the combination of wavelengths yielded complete inactivation after three minutes, compared to 25 minutes when 275 nm UVC light at 50% irradiation was used (See FIG. 18, line 1802).

In this way, the use of two or more wavelengths of light together (e.g., 275 nm and 365 nm) allowed for a synergistic interaction, enabling faster and complete inactivation. The effect of using combined wavelengths concurrently was greater than the sum of the effects of each wavelength sequentially as seen from FIGS. 18 and 19. The reduced intensities and exposure time enable an operational advantage by extending the lifetime of the bio-inactivation device.

The concurrent use of multiple UV and/or other wavelengths may enable more efficient and complete inactivation of microorganisms and other contaminants. Real-time reflectance and/or fluorescence feedback may also be used to affect adjustment of the operating parameters (e.g., exposure time and/or intensity level), to achieve complete and rapid inactivation.

The technical effect of multi-wavelength light exposure by the various depicted embodiments of the bio-inactivation device includes irreversible inactivation of both molecular contaminants and biological organisms. Operation of the bio-inactivating device may enable sterilization of reagents and disinfect laboratory surfaces, making them suitable for reproducible and accurate high-throughput amplification and/or sequencing methods. Additionally, it may further eliminate false positive results by increasing signal-to-noise ratio (SNR).

An example provides for a microplate irradiation system, including a housing, a chamber within the housing and configured to house a microplate; and a modular light engine positioned in the housing above the chamber, the modular light engine including one or more light emitting devices configured to emit radiation directed to a top surface of the microplate when the microplate is positioned in the chamber. In a first example, the chamber is formed in part by a drawer configured to move in and out of the housing, the drawer comprising a stage to hold the microplate. In a second example, which optionally includes the first example, each light emitting device comprises an array of light emitting diodes coupled to a substrate. In a third example, which optionally includes one or more of each of the first and second examples, each array of light emitting diodes comprises a first set of light emitting diodes evenly spaced in a first row and a second set of light emitting diodes evenly spaced in a second row. In a fourth example, which optionally includes one or more of each of the first through third examples, each array of light emitting diodes comprises exactly sixteen light emitting diodes. In a fifth example, which optionally includes one or more of each of the first through fourth examples, the modular light engine comprises exactly seven light emitting devices. In a sixth example, which optionally includes one or more of each of the first through fifth examples, each substrate is coupled to one or more cooling fins. In a seventh example, which optionally includes one or more of each of the first through sixth examples, the housing includes a vent, and the system further includes a fan configured to circulate air from the vent and across the one or more cooling fins. In an eighth example, which optionally includes one or more of each of the first through seventh examples, when the microplate is positioned in the chamber, each array of light emitting diodes is positioned intermediate the microplate and the respective one or more cooling fins. In a ninth example, which optionally includes one or more of each of the first through eighth examples, each light emitting device comprises exactly three cooling fins. In a tenth example, which optionally includes one or more of each of the first through ninth examples, the system further including a controller storing non-transitory instructions executable to adjust one or more of an intensity of light output by each light emitting diode and a duration of light output by each light emitting diode. In an eleventh example, which optionally includes one or more of each of the first through tenth examples, each light emitting diode is configured to output light of a single, common wavelength. In a twelfth example, which optionally includes one or more of each of the first through eleventh examples, a first subset of light emitting diodes is configured to output light of a first wavelength and a second subset of light emitting diodes is configured to output light of a second, different wavelength.

Another example provides a method of irradiating a treatment surface with a bio-inactivation device, including activating a first light emitting device of the bio-inactivation device to emit germicidal light of a first wavelength toward the treatment surface, and activating a second light emitting device of the bio-inactivation device to emit germicidal light of a second, different wavelength toward the treatment surface. In a first example, the first wavelength is 275 nm and the second wavelength is 365 nm. In a second example, which optionally includes the first example, the method further includes deactivating the first light emitting device and the second light emitting device based on feedback from a photodetector of the bio-inactivation device.

An example provides a bio-inactivation device including a first light emitting device configured to emit germicidal light of a first wavelength; a second light emitting device configured to emit germicidal light of a second wavelength; a photodetector; and a controller storing non-transitory instructions executable to: activate the first light emitting device and the second light emitting device to emit light of the first wavelength and the second wavelength at a treatment surface; and deactivate the first light emitting device and second light emitting device based on output from the photodetector. In a first example, the photodetector is configured to detect light reflected from the treatment surface, and wherein the instructions are executable to deactivate the first light emitting device and the second light emitting device responsive to the output from the photodetector indicating that an amount of light reflected from the treatment surface has changed by a threshold amount. In a second example, which optionally includes the first example, the photodetector is configured to detect fluorescence emitted from one or more contaminants on the treatment surface, and the instructions are executable to deactivate the first light emitting device and the second light emitting device responsive to the output from the photodetector indicating that an amount of fluorescence emitted from the one or more contaminants on the treatment surface has changed by a threshold amount. In a third example, which optionally includes one or more or both of the first and second examples, the first light emitting device comprises one or more light emitting diodes configured to output light at 275 nm and the second light emitting device comprises one or more light emitting diodes configured to output light at 365 nm.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 1-11, 13, and 14 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An irradiation system, including:
    a housing;
    a chamber within the housing and configured to house an apparatus; and
    a modular light engine positioned in the housing above the chamber, the modular light engine including:
        a first light emitting device comprising one or more light emitting diodes configured to output light of a first wavelength;
        a second light emitting device comprising one or more light emitting diodes configured to output light of a second wavelength;
        a photodetector; and
        a controller storing non-transitory instructions executable to:
            emit light of the first wavelength at a treatment surface with the first light emitting device;
            determine, based on feedback from the photodetector, that a change in fluorescence of the treatment surface is greater than a first threshold but less than a second threshold, and in response, switch to emitting light of the second wavelength at the treatment surface with the second light emitting device; and
            determine, based on the feedback from the photodetector, that the change in fluorescence of the treatment surface is greater than the second threshold, and in response deactivate the second light emitting device.

2. The system of claim 1, wherein the chamber is formed in part by a drawer configured to move in and out of the housing, the drawer comprising a stage to hold the apparatus.

3. The system of claim 1, wherein each of the first light emitting device and the second light emitting device comprises an array of light emitting diodes coupled to a substrate.

4. The system of claim 3, wherein each array of light emitting diodes comprises a first set of light emitting diodes evenly spaced in a first row and a second set of light emitting diodes evenly spaced in a second row.

5. The system of claim 3, wherein each array of light emitting diodes comprises exactly sixteen light emitting diodes.

6. The system of claim 3, wherein the modular light engine comprises exactly seven light emitting devices.

7. The system of claim 3, wherein each substrate is coupled to one or more cooling fins.

8. The system of claim 7, wherein the housing includes a vent, and further comprising a fan configured to circulate air from the vent and across the one or more cooling fins.

9. The system of claim 7, wherein when the apparatus is positioned in the chamber, each array of light emitting diodes is positioned intermediate the apparatus and the respective one or more cooling fins.

10. The system of claim 7, wherein each of the first light emitting device and the second light emitting device comprises exactly three cooling fins.

11. The system of claim 3, wherein the non-transitory instructions are executable to adjust one or more of an intensity of light output by each light emitting diode and a duration of light output by each of the light emitting diodes.

12. The system of claim 3, wherein each of the light emitting diodes is configured to output light of a single, common wavelength.

13. The system of claim 3, wherein a first subset of light emitting diodes is configured to output light of a first wavelength and a second subset of light emitting diodes is configured to output light of a second, different wavelength.

* * * * *